US008674706B2

(12) United States Patent
Peschmann et al.

(10) Patent No.: US 8,674,706 B2
(45) Date of Patent: Mar. 18, 2014

(54) METHODS AND SYSTEMS FOR THE RAPID DETECTION OF CONCEALED OBJECTS

(75) Inventors: Kristian R. Peschmann, Torrance, CA (US); Kenneth Robert Mann, Surrey (GB)

(73) Assignee: Rapiscan Systems, Inc., Torrance, CA (US)

( * ) Notice: Subject to any disclaimer, the term of this patent is extended or adjusted under 35 U.S.C. 154(b) by 205 days.

(21) Appl. No.: 13/368,020

(22) Filed: Feb. 7, 2012

(65) Prior Publication Data

US 2012/0213331 A1    Aug. 23, 2012

Related U.S. Application Data

(60) Continuation of application No. 12/505,659, filed on Jul. 20, 2009, now Pat. No. 8,138,770, which is a continuation of application No. 12/175,599, filed on Jul. 18, 2008, now Pat. No. 7,579,845, which is a division of application No. 10/952,665, filed on Sep. 9, 2004, now Pat. No. 7,417,440, which is a continuation-in-part of application No. 10/662,778, filed on Sep. 15, 2003, now abandoned.

(51) Int. Cl.
  *G01R 27/04*    (2006.01)
  *G01N 23/04*    (2006.01)

(52) U.S. Cl.
  USPC ............................................. 324/637; 378/57

(58) Field of Classification Search
  USPC .......... 324/637, 638, 639, 642; 250/250, 582; 378/57; 340/540, 691.1
  See application file for complete search history.

(56) References Cited

U.S. PATENT DOCUMENTS

| | | | |
|---|---|---|---|
| 2,299,251 | A | 10/1942 | Perbal |
| 2,831,123 | A | 4/1958 | Daly |
| 3,707,672 | A | 12/1972 | Miller et al. |
| 3,713,156 | A | 1/1973 | Pothier |
| 3,766,387 | A | 10/1973 | Heffan et al. |
| 3,784,837 | A | 1/1974 | Holmstrom |
| RE28,544 | E | 9/1975 | Stein et al. |
| 4,047,035 | A | 9/1977 | Dennhoven et al. |
| 4,122,783 | A | 10/1978 | Pretini |
| 4,139,771 | A | 2/1979 | Dennhoven et al. |
| 4,210,811 | A | 7/1980 | Dennhoven et al. |
| 4,216,499 | A | 8/1980 | Kunze et al. |
| 4,366,382 | A | 12/1982 | Kotowski |
| 4,399,403 | A | 8/1983 | Strandberg et al. |

(Continued)

OTHER PUBLICATIONS

Sheen, David et al. "Three-Dimensional Millimeter-Wave Imaging for Concealed Weapon Detection", Sep. 2001, IEEE Transactions on Microwave Theory and Techniques, vol. 49, No. 9, pp. 1581-1592.

*Primary Examiner* — Hoai-An D Nguyen
(74) *Attorney, Agent, or Firm* — Novel IP

(57) ABSTRACT

The present invention provides for an improved scanning process having microwave arrays comprised of microwave transmitters in radiographic alignment with microwave receivers. The microwave array emits controllably directed microwave radiation toward an object under inspection. The object under inspection absorbs radiation in a manner dependent upon its metal content. The microwave radiation absorption can be used to generate a measurement of metal content. The measurement, in turn, can be used to calculate at least a portion of the volume and shape of the object under inspection. The measurement can be compared to a plurality of predefined threats. The microwave screening system is used in combination with other screening technologies, such as NQR-based screening, X-ray transmission based screening, X-ray scattered based screening, or Computed Tomography based screening.

20 Claims, 25 Drawing Sheets

(56) References Cited

U.S. PATENT DOCUMENTS

| | | |
|---|---|---|
| 4,430,568 A | 2/1984 | Yoshida et al. |
| 4,471,343 A | 9/1984 | Lemelson |
| 4,566,113 A | 1/1986 | Donges et al. |
| 4,599,740 A | 7/1986 | Cable |
| 4,641,330 A | 2/1987 | Herwig et al. |
| 4,736,401 A | 4/1988 | Donges et al. |
| 4,754,469 A | 6/1988 | Harding et al. |
| 4,788,704 A | 11/1988 | Donges et al. |
| 4,825,454 A | 4/1989 | Annis et al. |
| 4,884,289 A | 11/1989 | Glockmann et al. |
| 4,956,856 A | 9/1990 | Harding |
| 4,975,968 A | 12/1990 | Yukl |
| 4,979,202 A | 12/1990 | Siczek et al. |
| 4,991,189 A | 2/1991 | Boomgaarden et al. |
| 5,008,911 A | 4/1991 | Harding |
| 5,022,062 A | 6/1991 | Annis |
| 5,065,418 A | 11/1991 | Bermbach et al. |
| 5,081,456 A | 1/1992 | Michiguchi et al. |
| 5,091,924 A | 2/1992 | Bermbach et al. |
| 5,098,640 A | 3/1992 | Gozani et al. |
| 5,179,581 A | 1/1993 | Annis |
| 5,181,234 A | 1/1993 | Smith |
| 5,182,764 A | 1/1993 | Peschmann et al. |
| 5,224,144 A | 6/1993 | Annis |
| 5,227,800 A | 7/1993 | Huguenin et al. |
| 5,237,598 A | 8/1993 | Albert |
| 5,247,561 A | 9/1993 | Kotowski |
| 5,253,283 A | 10/1993 | Annis et al. |
| 5,265,144 A | 11/1993 | Harding et al. |
| 5,313,511 A | 5/1994 | Annis et al. |
| 5,339,080 A | 8/1994 | Steinway et al. |
| 5,345,240 A | 9/1994 | Frazier |
| 5,367,552 A | 11/1994 | Peschmann |
| 5,379,334 A | 1/1995 | Zimmer et al. |
| 5,493,596 A | 2/1996 | Annis |
| 5,552,705 A | 9/1996 | Keller |
| 5,557,283 A | 9/1996 | Sheen et al. |
| 5,600,700 A | 2/1997 | Krug et al. |
| 5,638,420 A | 6/1997 | Armistead |
| 5,642,393 A | 6/1997 | Krug et al. |
| 5,642,394 A | 6/1997 | Rothschild |
| 5,666,393 A | 9/1997 | Annis |
| 5,687,210 A | 11/1997 | Maitrejean et al. |
| 5,689,239 A | 11/1997 | Turner et al. |
| 5,692,028 A | 11/1997 | Geus et al. |
| 5,751,837 A | 5/1998 | Watanabe et al. |
| 5,764,683 A | 6/1998 | Swift et al. |
| 5,768,334 A | 6/1998 | Maitrejean et al. |
| 5,787,145 A | 7/1998 | Geus |
| 5,805,660 A | 9/1998 | Perion et al. |
| 5,838,759 A | 11/1998 | Armistead |
| 5,903,623 A | 5/1999 | Swift et al. |
| 5,910,973 A | 6/1999 | Grodzins |
| 5,930,326 A | 7/1999 | Rothschild et al. |
| 5,940,468 A | 8/1999 | Huang et al. |
| 5,974,111 A | 10/1999 | Krug et al. |
| 6,026,135 A | 2/2000 | McFee et al. |
| 6,031,890 A | 2/2000 | Bermbach et al. |
| 6,054,712 A | 4/2000 | Komardin et al. |
| 6,058,158 A | 5/2000 | Eiler |
| 6,067,344 A | 5/2000 | Grodzins et al. |
| 6,081,580 A | 6/2000 | Grodzins et al. |
| 6,094,472 A | 7/2000 | Smith |
| 6,151,381 A | 11/2000 | Grodzins et al. |
| 6,184,841 B1 | 2/2001 | Shober et al. |
| 6,188,743 B1 | 2/2001 | Tybinkowski et al. |
| 6,188,747 B1 | 2/2001 | Geus et al. |
| 6,192,101 B1 | 2/2001 | Grodzins |
| 6,192,104 B1 | 2/2001 | Adams |
| 6,195,413 B1 | 2/2001 | Geus et al. |
| 6,198,795 B1 | 3/2001 | Naumann et al. |
| 6,216,540 B1 | 4/2001 | Nelson et al. |
| 6,218,943 B1 | 4/2001 | Ellenbogen |
| 6,249,567 B1 | 6/2001 | Rothschild et al. |
| 6,252,929 B1 | 6/2001 | Swift et al. |
| 6,256,369 B1 | 7/2001 | Lai |
| 6,278,115 B1 | 8/2001 | Annis et al. |
| 6,282,260 B1 | 8/2001 | Grodzins |
| 6,288,676 B1 | 9/2001 | Maloney |
| 6,292,533 B1 | 9/2001 | Swift et al. |
| 6,301,326 B2 | 10/2001 | Bjorkholm |
| 6,320,933 B1 | 11/2001 | Grodzins et al. |
| 6,342,696 B1 | 1/2002 | Chadwick |
| 6,356,620 B1 | 3/2002 | Rothschild et al. |
| 6,359,582 B1 | 3/2002 | MacAleese et al. |
| 6,417,797 B1 | 7/2002 | Cousins et al. |
| 6,424,695 B1 | 7/2002 | Grodzins et al. |
| 6,434,219 B1 | 8/2002 | Rothschild et al. |
| 6,435,715 B1 | 8/2002 | Betz et al. |
| 6,442,233 B1 | 8/2002 | Grodzins et al. |
| 645,300 A1 | 9/2002 | Adams et al. |
| 6,445,765 B1 | 9/2002 | Frank et al. |
| 6,453,003 B1 | 9/2002 | Springer et al. |
| 6,456,093 B1 | 9/2002 | Merkel et al. |
| 6,456,684 B1 | 9/2002 | Mun et al. |
| 6,459,761 B1 | 10/2002 | Grodzins et al. |
| 6,459,764 B1 | 10/2002 | Chalmers |
| 6,469,624 B1 | 10/2002 | Whan et al. |
| 6,473,487 B1 | 10/2002 | Le |
| RE37,899 E | 11/2002 | Grodzins et al. |
| 6,480,141 B1 | 11/2002 | Toth et al. |
| 6,483,894 B2 | 11/2002 | Hartick et al. |
| 6,501,414 B2 | 12/2002 | Arndt et al. |
| 6,507,025 B1 | 1/2003 | Verbinski et al. |
| 6,532,276 B1 | 3/2003 | Hartick et al. |
| 654,257 A1 | 4/2003 | Ries et al. |
| 6,542,574 B2 | 4/2003 | Grodzins |
| 6,542,580 B1 | 4/2003 | Carver et al. |
| 6,546,072 B1 | 4/2003 | Chalmers |
| 6,552,346 B2 | 4/2003 | Verbinski et al. |
| 6,563,903 B2 | 5/2003 | Kang et al. |
| 6,580,778 B2 | 6/2003 | Meder |
| 6,584,170 B2 | 6/2003 | Aust et al. |
| 6,597,760 B2 | 7/2003 | Beneke et al. |
| 6,606,516 B2 | 8/2003 | Levine |
| 6,636,581 B2 | 10/2003 | Sorenson |
| 6,650,276 B2 | 11/2003 | Lawless |
| 6,653,588 B1 | 11/2003 | Gillard-Hickman |
| 6,658,087 B2 | 12/2003 | Chalmers et al. |
| 6,663,280 B2 | 12/2003 | Doenges |
| 6,665,373 B1 | 12/2003 | Kotowski et al. |
| 6,665,433 B2 | 12/2003 | Roder |
| 6,763,635 B1 | 7/2004 | Lowman |
| 6,768,317 B2 | 7/2004 | Moller et al. |
| 6,785,357 B2 | 8/2004 | Bernardi et al. |
| 6,812,426 B2 | 11/2004 | Kotowski et al. |
| 6,816,571 B2 | 11/2004 | Bijjani et al. |
| 6,831,590 B1 | 12/2004 | Steinway et al. |
| 6,837,422 B1 | 1/2005 | Meder |
| 6,839,403 B1 | 1/2005 | Kotowski et al. |
| 6,843,599 B2 | 1/2005 | Le et al. |
| 6,856,271 B1 | 2/2005 | Hausner |
| 6,876,322 B2 | 4/2005 | Keller |
| 6,891,381 B2 | 5/2005 | Bailey et al. |
| 6,894,636 B2 | 5/2005 | Anderton et al. |
| 6,920,197 B2 | 7/2005 | Kang et al. |
| 7,039,159 B2 | 5/2006 | Muenchau et al. |
| 7,207,713 B2 | 4/2007 | Lowman |
| 7,606,348 B2 * | 10/2009 | Foland et al. .................. 378/57 |
| 7,831,012 B2 * | 11/2010 | Foland et al. .................. 378/9 |
| 2002/0008655 A1 | 1/2002 | Haj-Yousef |
| 2003/0009202 A1 | 1/2003 | Levine |
| 2003/0179126 A1 | 9/2003 | Jablonski |
| 2003/0216644 A1 | 11/2003 | Hall |
| 2004/0077943 A1 | 4/2004 | Meaney et al. |
| 2004/0141584 A1 | 7/2004 | Bernardi et al. |
| 2006/0145771 A1 | 7/2006 | Strange |

* cited by examiner

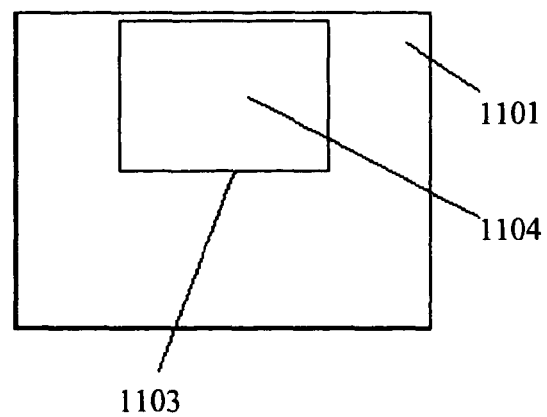
Figure 11(a) FRONT VIEW
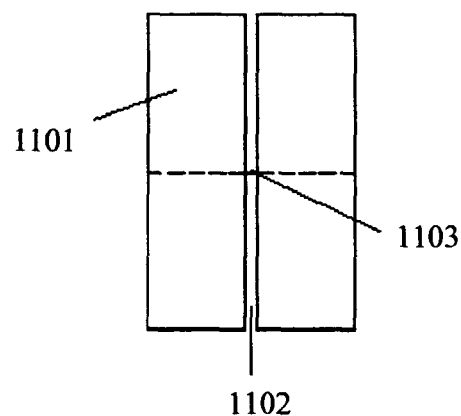
Figure 11(b) SIDE VIEW

METHODS AND SYSTEMS FOR THE RAPID DETECTION OF CONCEALED OBJECTS

CROSS-REFERENCE TO RELATED APPLICATION(S)

This application is a continuation of U.S. patent application Ser. No. 12/505,659, filed on Jul. 20, 2009 and issued on Mar. 20, 2012 as U.S. Pat. No. 8,138,770, which is a continuation of U.S. patent application Ser. No. 12/175,599, filed on Jul. 18, 2008 and issued on Aug. 25, 2009 as U.S. Pat. No. 7,579,845, which is a divisional of U.S. patent Ser. No. 10/952,665, filed on Sep. 9, 2004 and issued as U.S. Pat. No. 7,417,440, which is a continuation-in-part of U.S. patent application Ser. No. 10/662,778, filed on Sep. 15, 2003 and abandoned.

FIELD OF THE INVENTION

The present invention relates generally to a microwave imaging system that is compatible with X-ray and Nuclear Quadrupole Resonance (NQR) based methods and systems for detection of concealed threats, and threat resolution, and more specifically to improved methods and systems, using dual stage scanning to process luggage for faster inspection with reduced false alarm rate.

BACKGROUND OF THE INVENTION

Conventional X-ray systems produce radiographic projection images, which are then interpreted by an operator. These radiographs are often difficult to interpret because objects are superimposed. A trained operator must study and interpret each image to render an opinion on whether or not a target of interest, a threat, is present. With a large number of such radiographs to be interpreted, and with the implied requirement to keep the number of false alarms low, operator fatigue and distraction can compromise detection performance.

Advanced technologies, such as dual-energy projection imaging and Computed Tomography (CT), are being used for contraband detection, beyond conventional X-ray systems. In dual-energy imaging it is attempted to measure the effective atomic numbers of materials in containers such as luggage. However, the dual-energy method does not readily allow for the calculation of the actual atomic number of the concealed 'threat' itself, but rather yields only an average atomic number that represents the mix of the various items falling within the X-ray beam path, as the contents of an actual luggage is composed of different items and rarely conveniently separated. Thus dual-energy analysis is often confounded. Even if the atomic number of an item could be measured, the precision of this measurement would be compromised by X-ray photon noise to the extent that many innocuous items would show the "same" atomic number as many threat substances, and therefore the atomic number in principle cannot serve as a sufficiently specific classifier for threat versus no threat.

In X-ray CT cross-sectional images of slices of an object are reconstructed by processing multiple attenuation measurements taken at various angles around an object. CT images do not suffer much from the super-positioning problem present in standard radiographs. However, conventional CT systems take considerable time to perform multiple scans, to capture data, and to reconstruct the images. The throughput of CT systems is generally low. Coupled with the size and expense of CT systems this limitation has hindered CT use in applications such as baggage inspection where baggage throughput is an important concern. In addition, CT alarms on critical mass and density of a threat, but such properties are not unique to explosives. CT based systems suffer from high false alarm rate. Any such alarm is then to be cleared or confirmed by an operator, again interpreting images, or hand searching.

Apart from X-ray imaging systems, detection systems based on X-ray diffraction, or coherent scatter are also known. Their primary purpose is not to acquire images but to obtain information about the molecular structure of the substances an object is composed of. The so-called diffraction or coherent scatter signature is based on BRAGG reflection, that is the interference pattern of X-ray light, which develops when X-rays are reflected by the molecular structure or electron density distribution of a substance.

Various inspection region geometries have been developed and disclosed. Kratky, in Austrian Patent No. 2003753 publishes a refined arrangement of circular concentric apertures combined with an X-ray source and a point detector, to gain the small angle diffraction signature of an object placed between the apertures. More recently Harding in U.S. Pat. No. 5,265,144, uses a similar geometry but replaces the point shaped detector aperture with an annular detector configurations. Both patents are incorporated herein by reference.

The resulting diffraction spectra can be analyzed to determine the molecular structure of the diffracting object, or at least to recognize similarity with any one of a number of spectra, which have previously been obtained from dangerous substances.

One approach to detecting explosives in luggage was disclosed in British patent No. 2,299,251 in which a device uses Bragg reflection from crystal structures to identify crystalline and poly-crystalline substances. Substances can be identified because the energy spectrum distribution of the polychromatic radiation reflected at selected angles is characteristic of the crystal structure of the substance reflecting the radiation.

U.S. Pat. Nos. 4,754,469, 4,956,856, 5,008,911, 5,265,144, 5,600,700 and 6,054,712 describe methods and devices for examining substances, from biological tissues to explosives in luggage, by recording the spectra of coherent radiation scattered at various angles relative to an incident beam direction. U.S. Pat. No. 5,265,144 describes a device using concentric detecting rings for recording the radiation scattered at particular angles. Each of the prior art systems and methods, however, suffer from low processing rates because the scatter interaction cross sections are relatively small and the exposure times required to obtain useful diffraction spectra are long, in the range of seconds and minutes. For security inspections, equipment performance has to combine high detection sensitivity and high threat specificity with high throughput, at the order of hundreds of bags per hour.

U.S. Pat. No. 5,182,764 discloses an apparatus for detecting concealed objects, such as explosives, drugs, or other contraband, using CT scanning. To reduce the amount of CT scanning required, a pre-scanning approach is disclosed. Based upon the pre-scan data, selected locations for CT scanning are identified and CT scanning is undertaken at the selected locations. The inventors claim the pre-scan step reduces the scanning time required for each scanned item, therefore increasing throughput. However, the use of CT scanning is still inefficient, not threat specific, and does not allow for rapid scanning of objects.

U.S. Pat. No. 5,642,393 discloses a multi-view X-ray inspection probe that employs X-ray radiation transmitted through or scattered from an examined item to identify a suspicious region inside the item. An interface is used to receive X-ray data providing spatial information about the suspicious region and to provide this information to a selected material sensitive probe. The material sensitive probe, such as a coherent scatter probe, then acquires material specific information about the previously identified suspicious region and provides it to a computer. The disclosed system does not, however, address critical problems that arise in the course of applying a scatter probe to a selected suspicious region, including the accurate identification of a suspicious region, correction of detected data, and the nature of processing algorithms used.

Nuclear quadrupole resonance (NQR) is a contraband material detection device, which has applications in security screening. This technology has shown potential for the detection of a range of materials, in particular it is very effective for the detection of the types of explosives which can be the most challenging to detect using x-rays or CT machines. One potential weakness of the technique is that, with carefully designed electromagnetic shielding, the materials which it is being used to detect can be rendered undetectable. This potential problem is mitigated by the fact that such shielding consists of conductive (typically metal) volumes that must completely encapsulate the item to be detected. Because the items being searched for typically have a size large in comparison with most metal clutter (i.e. keys, coins, zippers, etc) the counter measure can be detected using a variety of metal detection techniques. However, the presence of a conductive loop around luggage means that the simplest forms of inductive metal detector would have limited performance.

Accordingly, there is need for an improved automatic threat detection and resolution system that captures data through an X-ray system and utilizes this data to identify threat items in a rapid, yet accurate, manner. There is also a need for determining the presence of potential shields of explosive materials. There is additionally a need to determine the shielding's size, volume, and position. Furthermore, there is a need for such detection technology to operate within enclosed metallic tunnels. Additionally, the system should provide for greater accuracy in utilizing pre-scan data to identify an inspection region and in processing scan data.

SUMMARY OF THE INVENTION

One object of the present invention is to provide for an improved scanning process having a first stage to pre-select the locations of potential threats and a second stage to accurately identify the nature of the threat. The improved scanning process increases throughput by limiting the detailed inspection to a small fraction of the total bag volume, and it decreases the frequency of false alarms by applying threat specific analysis.

Another object of the invention is to provide for improved processing techniques performed in association with various scanning systems. The improved processing techniques enable the substantially automated detection of threats and decrease the dependence on operator skill and performance.

Another object of the invention is to provide for a method and system to screen for relatively small amounts of threat material.

Another object of the invention is to provide for an improved method and system for screening for metal.

It is an object of the present invention to have a system that is relatively immune interference from metallic clutter items which are typical in bags and packages.

Yet another object of the present invention is to provide a system that is compact and compatible with being built into the structures typical for housing NQR equipment and X-ray or CT equipment.

A further object of the present invention is to provide a conductive volume imaging and detection system which is relatively insensitive to distortions in the image, owing largely to cross talk between different transmit and receive antenna pairs or microwave reflections caused by the presence of metallic clutter or reflections from the equipment housing the system.

A still further object of the present invention is to provide a system that uses an appropriate frequency of operation such that penetration is sufficient for the detection and imaging of objects within typical packages and bags but with a minimal amount of inaccuracies being introduced due to items with high dielectric loss being present within a bag.

A further object of the invention is to provide a system which will provide information which, either alone, or in conjunction with other metal detection techniques can be used to calculate the volume of any region encapsulated by conductive material.

A yet further object of the present invention is to provide a microwave detection and imaging system that can generate metal information in one, two or three axes for display. Images may be displayed for the microwave imaging system alone or overlaid with images from different imaging technologies such as computed tomography x-rays or transmission x-ray imaging systems.

A further object of the invention is a system that provides 3-dimensional positional information, which can be transmitted to complementary detection sensors that can be targeted at volumes within an object that cannot be screened effectively using NQR.

Accordingly, one embodiment of the present invention provides an apparatus for identifying an object concealed within a container. These objects may be considered threats, such as metal, an illegal drug, an explosive material, or a weapon. One embodiment is directed toward an integrated security scanning system, comprising a plurality of microwave arrays comprised of microwave transmitters in radiographic alignment with a plurality of microwave receivers, wherein said array is in physical communication with a housing and radiation shielding in physical communication with the housing. The microwave array emits controllably directed microwave radiation toward an object under inspection wherein said object under inspection absorbs radiation in a manner dependent upon its metal content. The microwave radiation absorption can be used to generate a measurement of metal content. The measurement, in turn, can be used to calculate at least a portion of the volume and shape of the object under inspection. The measurement can also be compared to a plurality of predefined threats.

In one embodiment, if the measurement is different than a pre-defined value, the object under inspection can be ignored by a system operator. Alternatively, if the measurement is different than a pre-defined value, the object under inspection can be selected for additional screening, such as NQR-based screening, X-ray transmission based screening, X-ray scattered based screening, or Computed Tomography based screening.

Optionally, the measurement can be used to generate a microwave image. The microwave image can be combined with an image produced by a technology selected from any one of NQR-based screening, X-ray transmission based screening, X-ray scattered based screening, or Computed Tomography based screening. The measurement can be used to generate positional information of metal content in the object under inspection. The positional information of metal content can be used to direct an analysis from material specific detection technology, such as X-ray diffraction, thermal neutron analysis or pulsed fast neutron analysis.

Optionally, the microwave transmitters and microwave receivers are configured in a plurality of different configurations, such as in a manner that replicates X-ray beam fan beam geometry, X-ray beam folded array geometry, or Computed Tomography array geometry. Optionally, the microwave transmitters are broad beam transmit antennas and microwave receivers are narrow band receive antennas. The broad beam transmit antennas are configured in parallel with said narrow band receive antennas. The broad beam transmit antennas are configured in parallel with said narrow band receive antennas and switched such that each transmit antenna transmits to several receive antennas. The switching occurs to move an illumination point around a region.

The present invention is also directed toward a method of scanning an object comprising the steps of subjecting the object to a first screening system comprising microwave arrays having at least one microwave transmitter in radiographic alignment with at least one microwave receiver and subjecting the object to a second screening system selected from any one of NQR-based screening, X-ray transmission based screening, X-ray scattered based screening, or Computed Tomography based screening. Optionally, first screening system operates concurrent with said second screening system or the first screening system operates serially with respect to said second screening system.

The present invention is also directed toward an integrated security scanning system, comprising a first screening system comprising microwave arrays having at least one microwave transmitter in radiographic alignment with at least one microwave receiver and a second screening system selected from any one of NQR-based screening, X-ray transmission based screening, X-ray scattered based screening, or Computed Tomography based screening. Optionally, the first screening system operates concurrent with said second screening system or the first screening system operates serially with respect to said second screening system.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following Detailed Description when considered in connection with the accompanying drawings, wherein:

FIGS. 11(a), 11(b) and 11(c) are projection drawings depicting a resonator body in a preferred NQR security system as used in the present invention;

DETAILED DESCRIPTION OF THE INVENTION

I. Introduction

The methods and systems described herein are directed towards finding, locating, and confirming threat items and substances. Such threats may comprise explosives such as C4, RDX, Semtex, Seismoplast, PE4, TNT, dynamite, PETN, ANFO among others, as well as other contraband such as drugs. Although the embodiments have been described in the context of a baggage inspection system, it should be evident to persons of ordinary skill in the art that items other than luggage such as other packages, mail, and cargo-containers, or even processed food stuffs, can also be analyzed and screened or graded and that the descriptions are exemplary and are not restrictive of the invention. Further, while the invention is described as a dual-stage system and method, the processing techniques discussed herein can be applied to each of the individual scanning stages.

II. An Overview of the Dual Stage System

Figure 1:
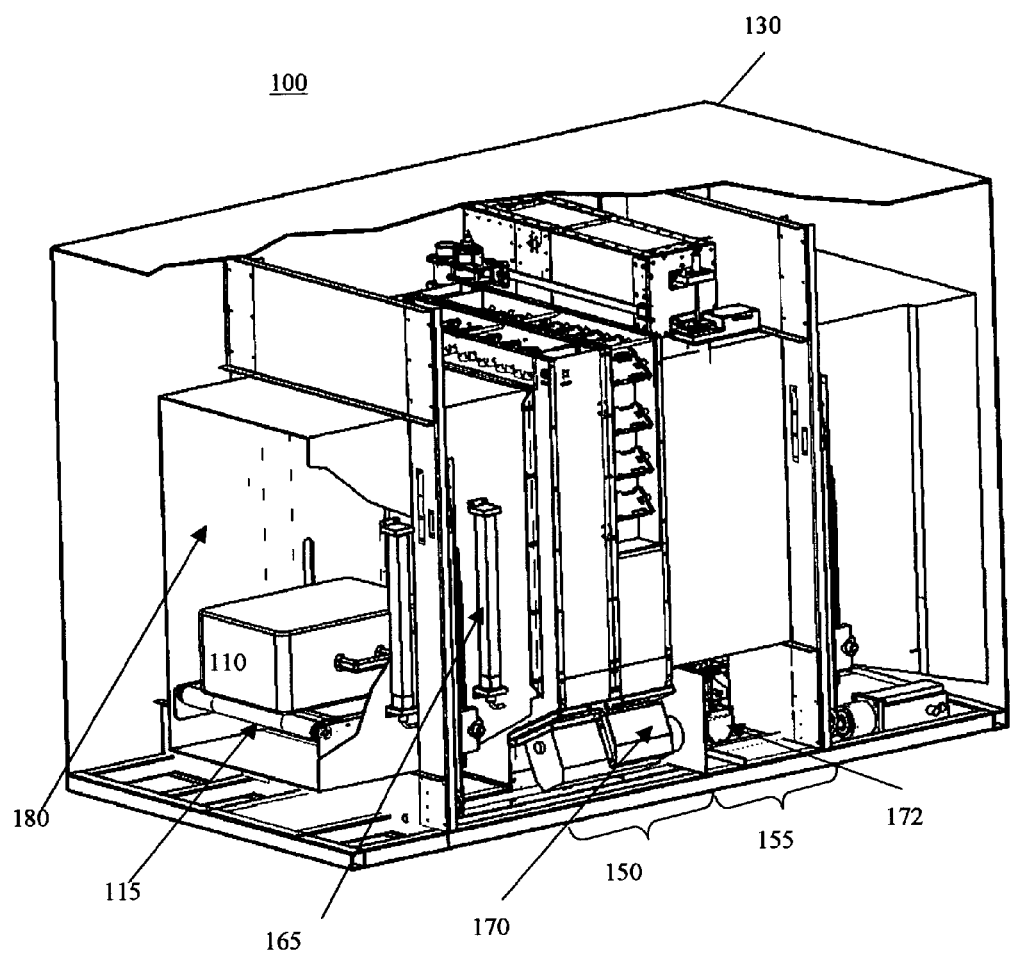
FIG. 1 is a schematic view of one embodiment of the dual stage X-ray scanning system.

Referring to FIG. 1, a dual stage scanning system 100 comprises a housing 130, which encompasses a conveyor system 115 for moving containers, baggage, luggage, or similar object 110 through a plurality of scanning stages 150, 155. A sensor system 165 is connected at the entrance to determine when an object being scanned 110 enters the scan field and communicates with a controller [not shown] to activate or deactivate an X-ray radiation source, 170, 172, as needed. A lead lined tunnel 180 surrounds the conveyor to reduce radiation leakage outside the equipment. At least one radiation source is not expressly depicted in FIG. 1 and would be visible if the system were viewed from the opposite side.

III. A Preferred Embodiment of the Dual Stage System of the Present Invention a. A Preferred First Stage Referring to FIG. 2, the first stage 150, comprises two X-ray cameras held together by a support structure 220, such as a frame or yoke, for stability. Each camera consists of an X-ray source 170, 171, a X-ray focusing means, such as a collimating slit comprised of a radio-opaque material, for example lead (not shown), and an array of detectors, 200, 201. In one embodiment, it is preferred that the detectors are configured into a L-shape in order to save space. One of ordinary skill in the art would appreciate that other folded configurations may be acceptable, provided that the detectors are appropriately positioned relative to the inspection region and X-ray source.

Figure 2:
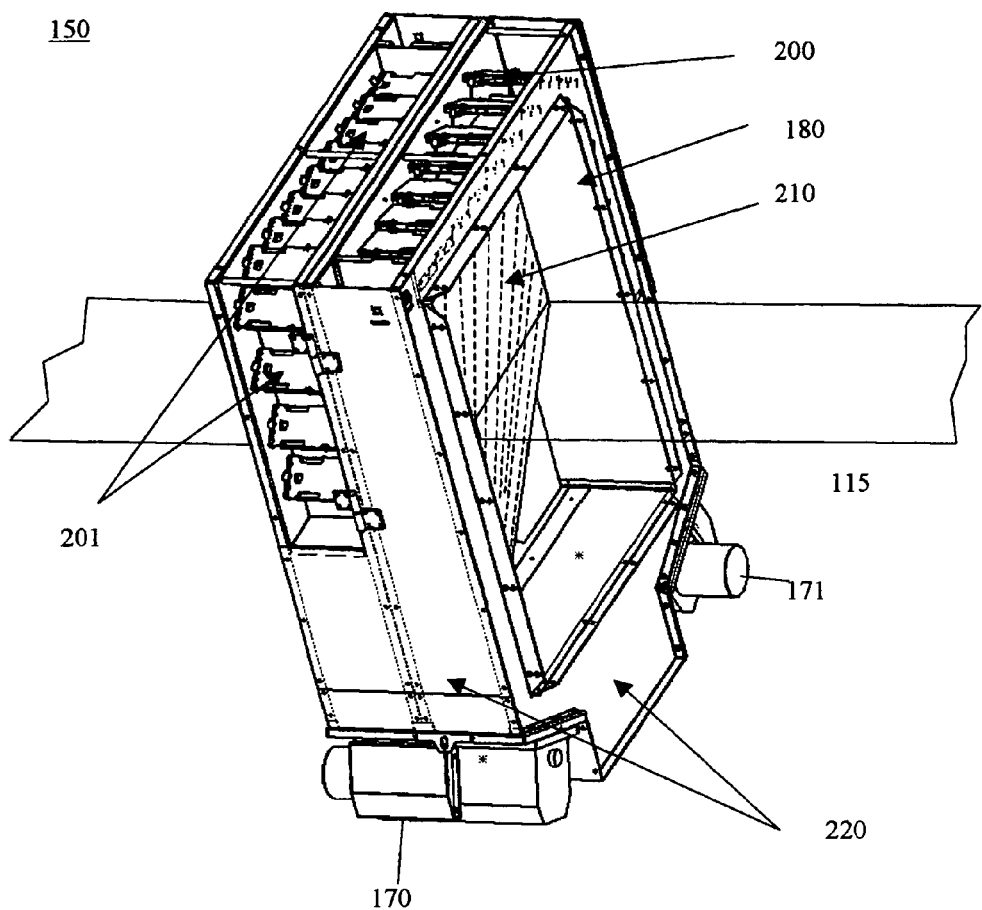
FIG. 2 is a schematic view of one embodiment of an X-ray scanning system for the first stage scanning system.

Behind each slit collimator, a thin sheet of X-rays 210 is formed. Within the sheet, a fan of pencil beams can be defined, shown as dashed lines in FIG. 2, by connecting lines between the stationary focus, not shown, and channels in the detector array. Between focus and detector is a tunnel 180 through which the luggage is transported or moved using any means known in the art, including, for example, a conveyor 115, the surface of which is depicted in FIG. 2. Wherever in the system radiation has to be transmitted from X-ray sources 170, 171 and through the region defined by tunnel 180, the conveyor belt support structure as well as the tunnel has windows constructed from materials essentially translucent to X-rays. The collimating slits and detector arrays are oriented so that the radiation-fans intersect the main conveyor surface within a few degrees of perpendicular relative to the conveyor surface. The two X-ray sources and their fans point in different directions.

In one preferred embodiment, the detector arrays are mounted on printed circuit boards with a vector positioned normal to their surfaces directed to the X-ray focus. An exemplary printed circuit board has a capacity of 64 channels, and the boards are physically arranged in Venetian blind configuration. The detector arrays consist of linear arrays of silicon photodiodes that are covered with scintillation material, which produces light when exposed to X-rays. The light is detected by the photodiodes that produce corresponding photo current signals. The detectors measure to what degree the X-ray signal has attenuated due to passing through a defined inspection volume. Specifically, the detected data are converted to digital format, corrected for detector gain and offset, and then stored. The required processor means may comprise computing hardware, firmware and/or software known to persons of ordinary skill in the art. When a container under inspection is moving through the tunnel and passing through the X-ray projections, both detector arrays are being sampled repetitively between 50 and 500 times per second. Displaying the line projections on a monitor renders the projection X-ray image.

While a conventional line scan system could be used as the first stage scanning system, it is preferred to use the system as described herein. More specifically, the present invention provides for the placement of at least two X-ray sources such that the directions of the X-ray projections emanating from the sources are mirrored relative to the central vertical plane. Therefore, from the perspective of a view along the path of conveyance through the first stage scanning system, at least one X-ray generator is mounted at a five o'clock position and at least one X-ray generator is mounted at the 7 o'clock position.

One of ordinary skill in the art would appreciate that the first stage scanning system is not limited to the specific embodiments described above and that other variations are included within the scope of this invention. In one alternative embodiment, detector arrays are expanded from a single array to multiple parallel arrays of detectors. In a second alternative embodiment, X-ray projections are taken using two-dimensional pixelated detector planes, without requiring the use of a conveyance means. It should be appreciated that, while the present invention will be further described using a description of the invention based on using the line scan configuration of single stationary foci and single line detector arrays in conjunction with a means of conveyance, the present invention includes other systems and methods that generate X-ray projection images and that such systems and methods can be used in the novel dual stage scanning system disclosed herein.

An alternative embodiment uses dual energy imaging. Dual energy imaging can be utilized to display an image where materials of a metallic constituency are suppressed (not displayed) or materials of an organic constituency are suppressed. Having the ability to selectively display certain materials within images helps reduce image clutter. For example, when inspecting containers for masses or explosives, which have little or no metallic component, the "organic materials only" display is preferred. The dual energy approach can be further refined to automatically discriminate between similar materials of higher and lower relative atomic numbers, such as between a plastic comprised of more lower atomic number atoms like hydrogen and carbon and a plastic comprised of more higher atomic number elements like oxygen and nitrogen; or between aluminum (atomic number 13) and steel (atomic number 26).

In one embodiment, dual energy data is generated by using an X-ray tube with extended spectral emission, which is standard, in conjunction with arrays of stacked detectors, where the first detector is positioned to detect more of the lower energy, or so-called softer X-ray photons, and the second detector is positioned to detect the balance of the energy, namely the higher energy, or so-called harder, photons. The second detector is typically positioned behind the first detector. The low energy and high energy measurements are combined in a suitable way using a series of calibration measurements derived from dual energy measurements taken of identified organic and metallic materials of known thicknesses and result in the display of images, including organic only or metal only images. One of ordinary skill in the art would appreciate that various dual energy line scan systems are commercially available.

It is preferred to use projection imaging as the first stage scanning step in this invention. Features shown in the projection images can be used by an operator to make a final decision on whether items identified in a container represent a threat of some type. Additionally, by taking projections from at least two different angles, it is possible to triangulate the location of a potential threat relative to the physical coordinates of the system and use those coordinates to perform a more specific and focused second stage scan. The triangulation process localizes certain items that generate features of interest in the images and identifies their location in the form of system coordinates.

To perform the triangulation process, the images that form the basis of the triangulation process and that are used to identify a target region are first identified. In one embodiment, the images are analyzed by an operator who visually and approximately determines a plurality of X-ray image characteristics, such as degree of attenuation and projected area, associated with mass, atomic number (identified using image color coding), and shape. Operators also use contextual information, such as an X-ray opaque organic mass in a transistor radio or a suspiciously thick suitcase wall. The analytical process is known to those of ordinary skill in the art and includes the interpretation of X-ray image characteristics.

In another embodiment, images are identified by determining the target regions automatically. For example, where the screening target is a mass of plastic explosive, known algorithms, working on dual energy X-ray projection image data, can be combined to automatically find such target. Examples for such algorithm components include, but are not limited to, edge detection, watershed, and connected component labeling.

Figure 3:
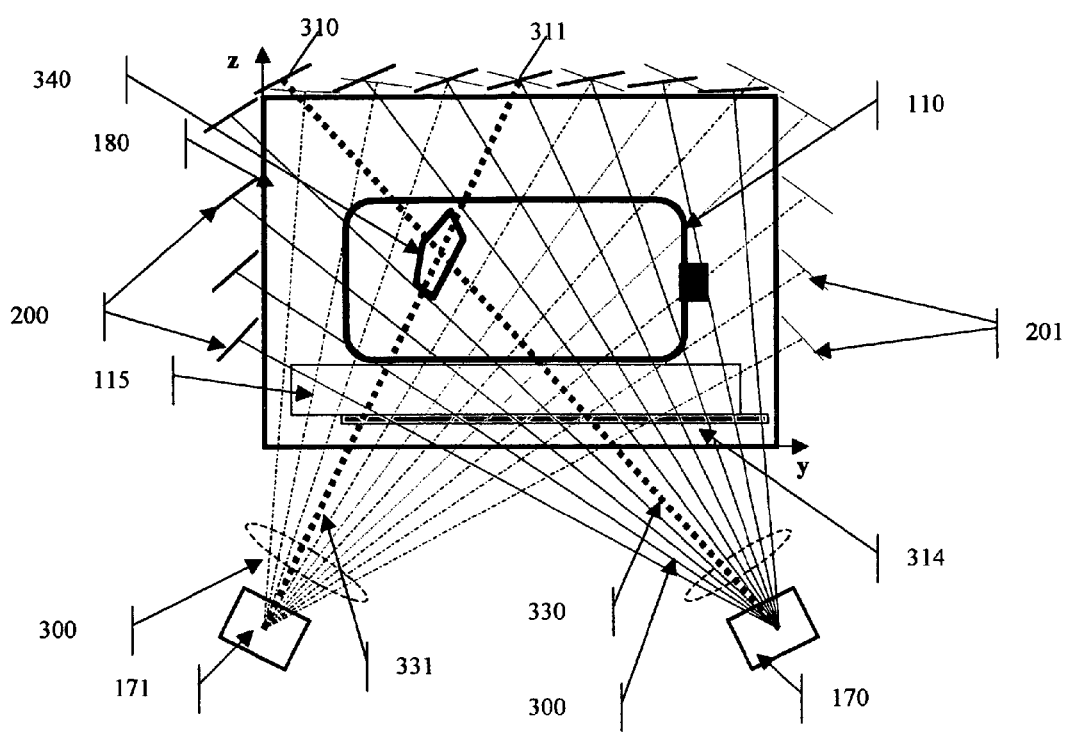
FIG. 3 is a schematic view of one embodiment of the first stage of the X-ray scanning system for identifying a target region.

Referring to FIG. 3, a container 110 is moved on a conveyor 115 through a tunnel 180 in x-direction, perpendicular to the plane of the Figure. A first X-ray generator 170, C1, with an X-ray emitting focus projects a fan of X-rays 300 through a slit collimator onto an array of detectors mounted on printed circuit boards 200. One of ordinary skill in the art would appreciate that only a small sampling of detectors are shown in FIG. 3 and that a typical system would have a far greater number of detectors, preferably 700 to 800, more preferably 740. As shown, the orientation of the fan plane is perpendicular to the conveyor surface. While a container is being moved along the conveyor surface, the detectors are read out repeatedly, and their signals are converted into digital format by detector electronics that are also mounted on the detector boards 200. The data are being processed and sorted further and stored in a computer [not shown] for display on a monitor [not shown]. Each horizontal line on the monitor corresponds to one particular detector in the array. Therefore, in a system using 740 detectors, the full image is composed of 740 lines.

A second X-ray camera, C2, consisting of X-ray generator 171, slit collimator (not shown) and detector array 201 is mounted in a different orientation, and offset in conveyor direction, by typically 100 mm. The detectors aligned with this camera are sampled essentially simultaneously with the detectors of the first camera and produce a second image displayed on a monitor.

Operationally, an item 340 located within the container 110 is recognized in the course of the first stage scan using a detection algorithm or by operator analysis, depending upon the system mode chosen. With the item 340 identified, the approximate centerline X-ray projections 330, 331 that pass through the object can be determined. Each of the centerlines 330, 331 is associated with a certain detector channel, 310 and 311 respectively in each view.

Figure 3A:
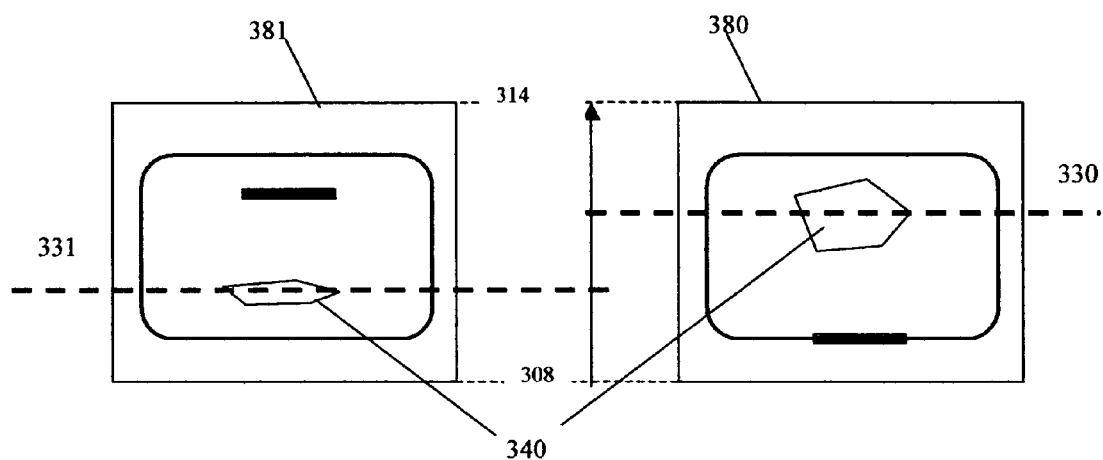
FIG. 3a depicts exemplary images for identifying the location of an item within a container.

Referring to FIG. 3a, once the detector channels have been determined, the location of the associated item 340 can be found in the y-z coordinate system. Two images 380, 381 corresponding to the two views are shown. With knowledge of the detectors associated with the centerlines 331, 330 and the range of detectors, 308 to 314, defined, the y and z coordinates of the item 340 can be derived. The x-coordinate is defined by the direction of conveyor motion and is known because the conveyor motion control system, timing of X-ray exposure, and the fixed offset of the two scan planes are known. The x-coordinate can, for example, be referenced to the beginning, or leading edge of the container, which can be detected by a light curtain or similar position-detecting device. In particular, the two images are referenced to each other precisely in the x-coordinate direction.

The purpose of this triangulation or localization of identified items in a container is to generate control commands that can be used to position and focus the inspection region or inspection volume of the second stage scanning system on the identified item. Therefore, the first inspection stage quickly locates potential threats and determines their coordinates, as referenced to the system, while the second stage focuses on better determining the nature of the identified potential threat. It should be appreciated that, because the first stage characterization of a threat is loosely based on features in X-ray images, it will locate, find, and label, as a potential threat, items which are innocuous, in addition to real threats. Therefore, the performance of a detection system based only on the first stage, as described, suffers from a high false alarm rate.

One of ordinary skill in the art would also appreciate that other elements of the first stage scanning system are not depicted in FIG. 1 but would be included in an implementation of the system. For example, a shielding curtain is positioned at both the entrance and exit of the system 100 to protect against radiation leakage to the surrounding environment. The system 100 is controlled by a data interface system and computer system that is capable of rapid, high data rate processing, is in data communication with storage media for the storage of scan data and retrieval of reference libraries, and outputs to a monitor having a graphics card capable of presenting images.

It should also be appreciated that a second stage scan may not be required. In one embodiment, radiographic images from the first stage scan are displayed on a computer monitor for visual inspection with target regions or potential threats identified. An operator may dismiss some of the identified regions or threats based on context, observation, or other analytical tools. If no threats are identified, the container is cleared to exit the inspection system without subjecting it to the second stage of scanning. However, if the operator is unable to resolve an area as being a non-threat, the area is identified as a target region.

b. The Second Stage

The second stage inspection or scanning system closely inspects the identified target locations by deriving more specific information, or a signature, and confirming the first stage threat alarm only if the obtained signature matches the signature of a threat substance or threat item. An alarm confirmed by the second stage system are then taken seriously by operators and indicate the need for further inspection, including, but not limited to, operator image interpretation, additional scanning, and/or hand searching the container.

In a preferred embodiment, the second stage scanning system uses diffracted or scattered radiation to determine the properties of a material, obtain a signature, and, accordingly, identify a threat. Diffracted or scattered radiation comprises photons that have experienced an interaction with the object under investigation. In the special case of small angle scattering, the majority of interactions are elastic or energy-conserving; specifically, the diffracted photon has the same energy as it had before the interaction, just its direction of propagation has changed. If the energy distribution of the scattered photons is being analyzed by an energy-dispersive detector system, which is commercially available, certain properties of the material causing the scatter are being encoded in the signature. Photons scattered under small angles are scattered selectively due to interference effects. Since the process does not change the energy of the photons the signal also contains the distribution of the primary radiation in a simply multiplicative way. The incoming primary radiation, as well as the scattered radiation, encounter further spectral modifications due to other types of interactions, such as Compton scatter and photoelectric absorption, which are not energy preserving. If one wants to view the characteristics of the scattering material, other distracting spectral effects have to be removed.

The detected signature of a threat is therefore a combination of X-ray properties. One important property is a BRAGG diffraction spectrum, observed at small diffraction angles between 2 and 8 degrees, with a preferred value around 3 degrees.

Figure 4:
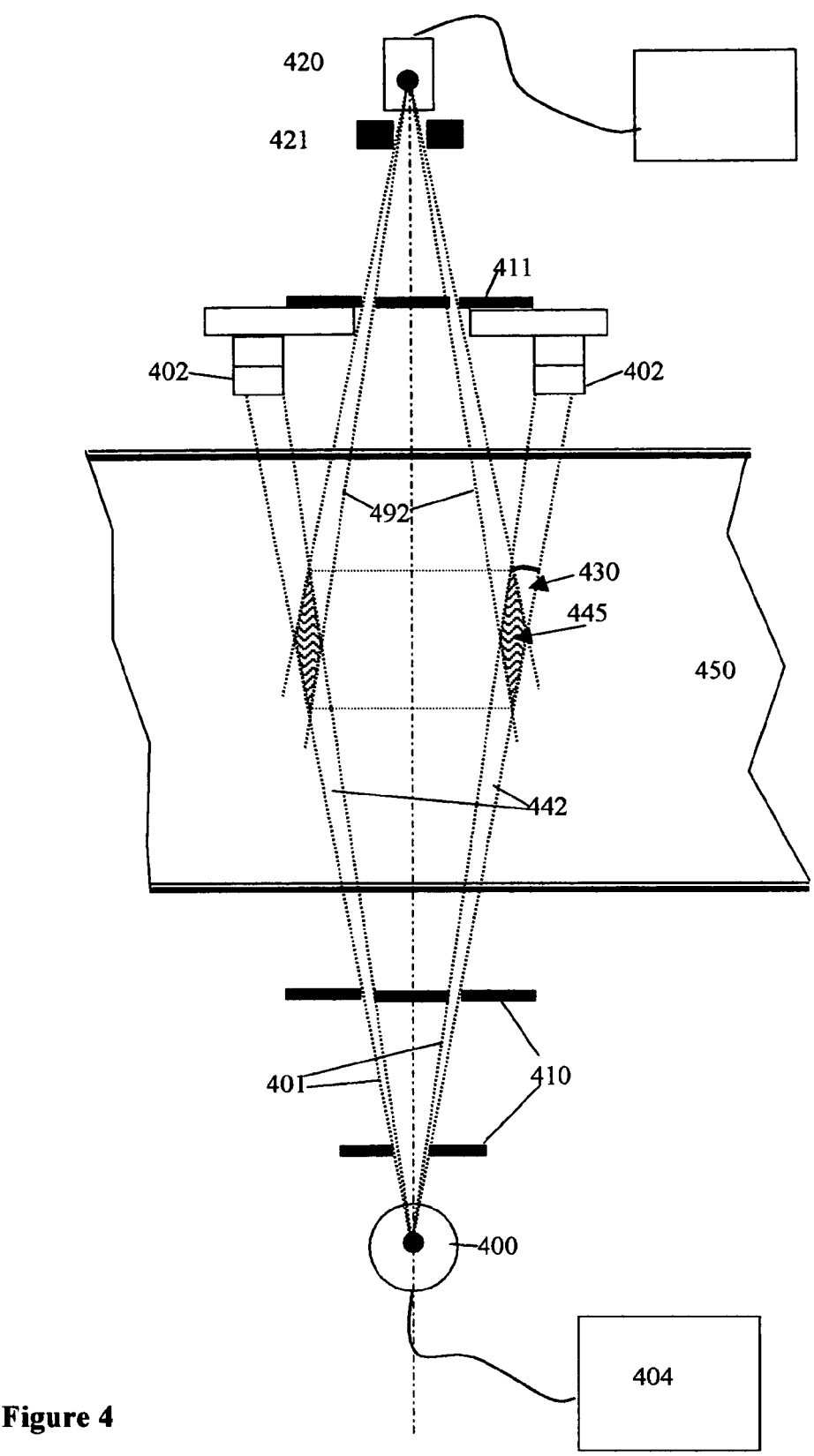
FIG. 4 is a schematic diagram of a cross-section of one embodiment of a preferred beam delivery system for use in a second stage scanning system.

FIG. 4 shows schematically a cross section of a preferred beam delivery system used to obtain BRAGG spectra at small angles. Other beam delivery systems can also be used in the present invention, including those disclosed by Kratky, et al. in Austrian Patent No. 2003753 and Harding in U.S. Pat. No. 5,265,144. The preferred system depicted in FIG. 4 further includes a transmission detector.

A beam delivery system separates the photon radiation emitted by the focus 400 of the X-ray source 404 into a plurality of beams. A beam 401 is formed by passing through apertures 410 and is directly detected by detectors 402, which are within the beam's direct line-of sight. These beams are referred to as transmission beams. Scatter interactions are detected by blocking direct line-of-sight detection through the use of ring apertures 410, 411 and exposing the associated detector 420 only to scattered radiation 492. Therefore, scatter radiation, generated when certain beams interact with an inspection region or volume 445, can be detected in the same apparatus as transmission radiation.

The choice of ring aperture diameters, distance to focus, and distance to detector determines the effective scatter angle 430 of the photons falling on the detector. In one embodiment, the scatter angle 430 is approximately the same for substantially all photons detected by the detector of the scattered radiation. It is preferred to configure the beam delivery system to establish an effective scatter angle of between two and 8 degrees. It is more preferable to have a scatter angle at or about 3 degrees. Using a beam delivery system having a circular symmetry has the advantage of obtaining a scatter contribution from a larger volume of the material being inspected, thereby increasing the inherently weak scatter signal. Additionally, the scatter spectrum can be cost efficiently detected using only a single detector channel 420 with an entrance aperture in the shape of a hole 421.

The scatter signal is generated by positioning the target region 445, identified in the first stage scan, between the beam forming apertures, irradiating that region 445 using the conical beam 442, and making sure scatter radiation from the target region 445 can be detected by the scatter detector. The target region 445, often contained within a container 450, is in the shape of a tube or ring 445 and is referred to as the inspection volume or inspection region. The length, diameter, and wall thickness of the inspection volume depends on the particular shape of the elements of the beam delivery system, including focus size, ring aperture diameter and width, detector opening and overall distance. In a preferred embodiment for the inspection of large luggage, the inspection volume is at or about 60 cubic centimeters.

Figure 5:
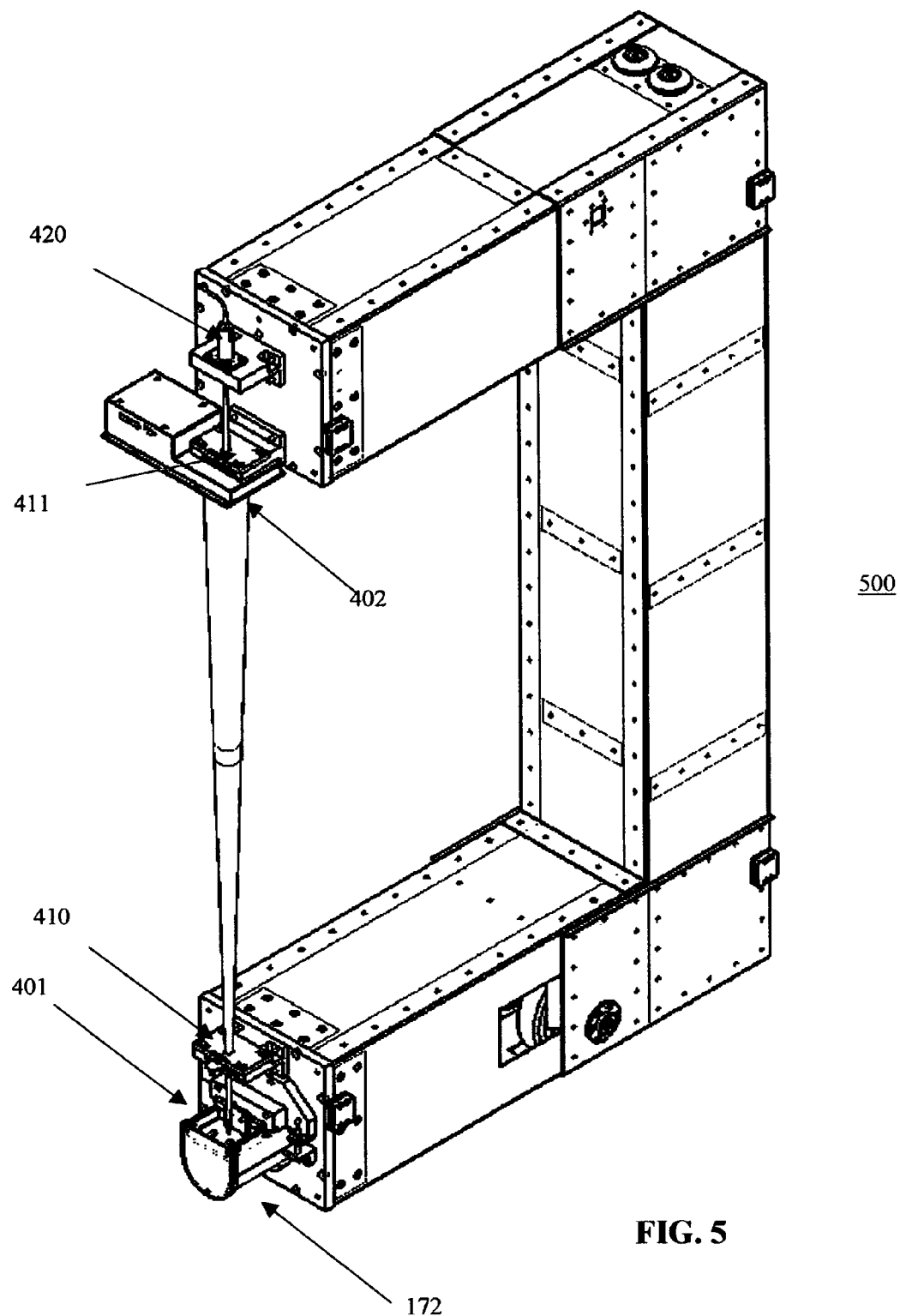
FIG. 5 is a schematic diagram of one embodiment of the beam delivery system of the second stage scanning system.

In a preferred embodiment, as shown in FIG. 5, the components of the beam delivery system are mounted to the open ends of a rigid support structure 500 formed in the shape of a C (referred to herein as a C-arm) and aligned with a tolerance of at or about 0.1 millimeters. A first arm of the C-arm comprises a X-ray tube with X-ray focus 172, a beam limiting aperture hole mounted to the tube head 401, and a ring-shaped aperture 410. A second arm holds comprises a transmission detector array 402, a second ring aperture 411, and an energy dispersive detector 420, equipped with an aperture hole.

The energy dispersive detector 420 is positioned to receive scattered radiation from a target object placed on the conveyor running between the arms of the C-arm support structure where a first arm is above the conveyor and a second arm is below the conveyor. The transmission detector is positioned to receive radiation attenuated by the same target object. It is preferable for the C-arm to be mobile and capable of moving in the x-direction along the length of the conveyor. Therefore, the C-arm with tube and detectors can be re-positioned along the length of the conveyor.

In a preferred embodiment, the scatter detector 420 is comprised of cadmium telluride or cadmium zinc telluride and is operated at room temperature, or approximate to room temperature, An exemplary embodiment is available from the eV Products Company, Saxonburg, Pa. This type of detector has a spectral resolution performance that is well matched to the limited angular requirements of this application, and therefore the limited spectral resolution of the beam delivery system.

In one mode of operation, the potential threat locations inside a container are found automatically by the first stage, and, based upon the physical coordinates obtained through triangulation, the second stage scanning system is automatically positioned to generate an inspection region that substantially overlaps with the identified target region. Where multiple threat locations are identified, the second stage scanning system is sequentially repositioned to focus on each subsequent target region. To scan each target region, the second stage X-ray source is activated and the scatter detector and transmission detector are sampled simultaneously. In a preferred embodiment, a transmission spectrum associated with the detected transmission data is characterized using a look up reference, figure, table, or chart, and the scatter spectrum is normalized using that identified transmission spectrum.

In another mode of operation, an operator actively identifies images that he or she believes corresponds to a potential threat. X-ray images from the first inspection stage are displayed to the operator, and the operator points to a suspicious object as it appears in both views. To support this functionality, operators use a computer system, comprising a mouse and monitor, to position cross hairs over the areas of interest on each of the images. Using coordinate data generated through triangulation, the second stage scanning system automatically positions itself such that an inspection region overlaps with the target region, activates the X-ray source and simultaneously samples the scatter detector and transmission detector. In a preferred embodiment, a transmission spectrum associated with the detected transmission data is characterized using a look up reference, figure, table, or chart, and the scatter spectrum is normalized using that identified transmission spectrum.

c. The Transmission Detectors

As discussed above, a transmission detector is integrally formed with the beam delivery system, as shown in FIGS. 4 and 5. A preferred transmission detector comprises a 16 channel array of dual energy detectors. The detector array further comprises pairs of detectors, including a low energy channel that receives and measures a first amount of radiation first (low energy) and a high energy channel that receives and measures a substantial portion of the balance of radiation (high energy). Dual energy detection has been described in connection with the linear scan arrays of the first inspection stage and is known to persons of ordinary skill in the art.

Figure 6:
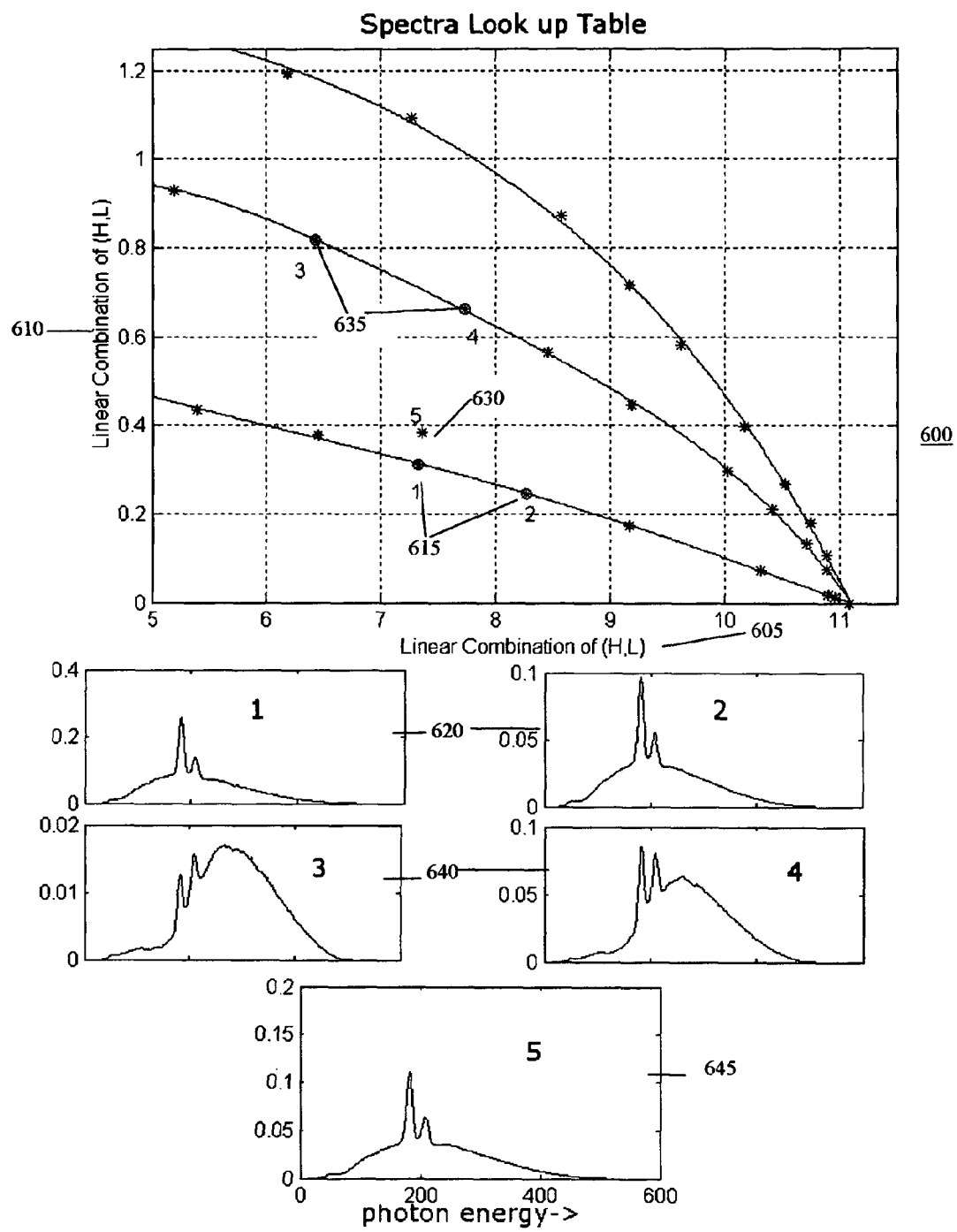
FIG. 6 is a schematic diagram of an exemplary look up source for transmission spectra.

The low energy and high energy detectors measure a plurality of low energy and high energy values that can be used to characterize the material being scanned. In a preferred embodiment, low energy and high energy data are used to reference a look up reference, figure, table, or chart (referred to as a look up source) which contains transmission spectra arranged in accordance with corresponding high and low energy values. The look up source is constructed with high energy values on one axis (i.e. the x-axis), and low energy values on a second axis (i.e. the y-axis). Referring to FIG. 6, an exemplary look up source 600 is shown. The source 600 is a graph with high energy values on the x-axis 605 and low energy values on the y-axis 610. Points 615 corresponding to measured spectra 620 are positioned on the graph according to certain linear combinations of the measured high and low dual energy detector signals on the x and y axis.

The transmission spectra used to normalize scatter data is therefore identified by obtaining high energy and low energy data values, identifying the point on the graph corresponding to the detected high and low energy values, and looking up the spectrum associated with that point. Where the detected high and low energy values yield a point on a graph that corresponds to an intermediate point 630 proximate to pre-established points 635, 615, a corresponding transmission spectra 645 can be calculated by performing a two-dimensional interpolation of the spectra 640, 620 associated with the pre-established points 635, 615.

To create the look up source, an exemplary approach places various materials of known composition and thickness, exposes them to X-ray sources, measures the resulting high and low energy data values, and uses the scatter detector to measure the corresponding transmission spectrum. More specifically, the beam path of the beam delivery system is modified to allow a direct beam from the focus through the pinhole to fall on the energy dispersive scatter detector. To further reduce the photon flux into a range that can be tolerated for energy-dispersive measurement, the current of the X-ray source is preferably reduced by a large factor, e.g. 100. Under these parameters, the scatter detector can be used to measure the transmission spectrum. Materials of known composition and thickness are placed in the beam path. The materials are exposed to X-ray radiation. Dual energy measurements are made using the dual energy detectors and a transmission spectrum is obtained using the scatter detector. Through this approach, for each material composition and thickness, a transmission spectrum is obtained and correlated with discrete pairs of dual energy transmission detector readings. This information is then arranged on a chart with the high energy value of the dual energy detector measurement on the x-axis, and the low energy value on the y-axis.

It should be appreciated that, in the disclosed embodiment, the spectra are the looked-up objects of the look up source. Instead of the spectra, however, the look up source can alternatively consist of spectral attenuation functions related to the attenuation of the materials placed in the beam when the look up source is being generated. The spectrum can then be obtained by multiplying one fixed spectrum, for example the spectrum measured without the material placed into the beam, with the spectral attenuation function retrieved from the look up source. Alternatively, the look-up source can contain numbers that are the parameters of analytical expressions, e.g. polynomials, which are formed to describe the attenuation functions in a parametric way.

The presently described approach is preferred because it enables the construction of a transmission detector array from lower cost materials, as opposed to constructing the array using more expensive energy dispersive detectors and support electronics. Moreover, it also addresses the difficult problem of using energy dispersive detectors to measure transmission spectra at the high flux rates that are experienced at the location of the transmission detector in the given configuration and at the same time at which the scatter data are recorded. The required strong attenuation of the transmission beams is a difficult problem that is avoided using the present invention. The look up table is an important element because the preferred dual energy detectors used in the transmission detector cannot deliver spectra directly.

As discussed, transmission spectra are being used to correct the scatter spectra that are being recorded by the energy dispersive detector. Normalizing scatter spectra with transmission spectra corrects for the confounding effects introduced by the specific spectral distribution of the primary radiation, as emitted from the X-ray source, as well as by spectrum-distorting effects known as beam hardening. To correct the scatter spectra, the detected scatter spectra are divided by the looked-up transmission spectra.

A normalized scatter spectrum exhibits a plurality of features. A first feature is that the location of the peaks and valleys of the spectrum are determined by the molecular structure of the materials located in the probe region. A second unrelated feature is that the average spectral signal of the normalized scatter signal, which can be of varying intensity, is linearly related to the gravimetric density of the material in the probe region. This can be used for threat discrimination since most explosives, particularly military explosives, have a density range above that of most other plastic or food items in suitcases.

In one embodiment, the normalized scatter signal is used to identify a threat item by comparing the obtained normalized scatter spectrum and/or spectral signal with a library of scatter signals from known threat items. This comparison can occur automatically by using a processor to compare a library of threat items, stored in a memory, with the obtained scatter signals. Such a library is developed by measuring the normalized scatter signatures of known threat items. In addition to using the transmission detector to generate data used to identify reference spectra, the transmission detector can function in a plurality of other ways. In one embodiment, the transmission detector acts as a position sensor. The transmission beam is interrupted or attenuated momentarily when an object on the conveyor crosses it. Tracking the moment of interruption can provide information on the physical position of the container on the conveyor and be used to appropriately position the beam delivery system or container.

In a second embodiment, the transmission detector array functions as an imaging detector to provide precise attenuation data for certain areas in containers, like container wall areas, where contraband can be hidden. When the circular beam is centered on an edge of a container, the edge of the container can be imaged in good detail, and can help analyze the edges for concealed threats.

In a third embodiment, transmission detector measurements can be used to determine whether the inspection region is, in fact, the same target region previously identified in the first stage scan. If the transmission data correlates with X-ray characteristics different than those obtained in the first stage scan, the relative positioning of the second stage scanning system and the object under inspection may be modified until the transmission data correlates with the same material characteristics that was identified in the first stage scan.

In a fourth embodiment, transmission detector data are also being used to simplify the algorithm-training procedure of the system, as described below, in particular the collection of threat material properties with irregularly shaped threat samples, like sticks of dynamite.

It should be noted that it would appear because the scatter radiation path and transmission path differ downstream from the scatter volume, there would be inconsistencies in the data when scatter and transmission data are combined. This inconsistency is one example of a number of partial volume effects, solutions for which are addressed herein. However, the inconsistencies are not significant and can be tolerated without encountering significant performance degradation of the system as a whole. As shown, FIG. 4 is not an isometric schematic and, in reality, the scatter angle is preferably about 3 degrees, and the real path differences are comparatively smaller.

d. Positioning Inspection Regions

As previously discussed, the second stage scanning system positions an inspection region to physically coincide with the target region identified in the first stage scan. The positioning means may be achieved using any method known in the art. In one embodiment, a plurality of control commands is produced in response to the determination of the location of the target region. The control commands are generated by at least one processor in data communication with a plurality of processors capable of executing the aforementioned triangulation techniques and/or determining the intersection of projection lines to identify the location of the target region in three dimensional system coordinates.

The control commands comprise data signals that drive a three-axis control system. The vertical position of the second-stage inspection volume can be adjusted to the target volume or region of the first stage scan by moving the conveyor system up or down. In another embodiment, the control commands comprise data signals that drive the adjustment of the beam delivery system in the second stage scanning system. The beam delivery system adjustment can include any type of adjustment to the collimation or beam focus, including the physical movement of a plurality of apertures horizontally, vertically, or diagonally, the physical modification of the diameter of the ring aperture by, for example, increasing or decreasing the aperture size. In another embodiment, the position of the support structure, or C-arm, can be modified along the conveyor direction to appropriately position the beam delivery system.

The second stage scan may be compromised when the volume of the target region is smaller than the inspection region of the second stage. In such cases, extraneous material, other than the material identified as being a potential threat, such as air, metal, or container edges, may be included. The resulting scatter radiation is therefore a function of multiple material types and may not be readily identifiable as being the signature of a single substance.

e. Threat Recognition Process of the Preferred Embodiment

In one embodiment, the present invention comprises a threat recognition process that incorporates a training methodology which relies on libraries in which threat signatures are obtained by combining the threat with other common materials, such as clothing, plastic, air, and metals. Specifically, the data used in training and developing the detection process are chosen to include data, which are corrupted by errors based on partial volume data from statistically varying containers and threat and non-threat material combinations. When the inspection volume is partially filled with a threat substance and partially filled with a second innocuous substance, a combination signal will be detected by the second scanning stage. The automatic threat recognition methodology recognizes the threat from the combination signal based upon the aforementioned training. An exemplary automatic threat recognition methodology, based on neural networks, is described below.

In a second embodiment, the detected scatter data is corrected for the effects of extraneous materials by preprocessing the data. The motion control system tracks where the inspection volume or region is located in relative to a specific reference point, such as the approximate outlines of the container, and relative to the conveyor system. Because of the ability to measure and track these reference points, the amount and portion of the inspection volume occupied by the conveyor structure can be determined. The conveyor structure includes the belt material as well as the structural member that is underneath the conveyor, which is referred to as the slider bed.

To correct the scatter spectrum for the presence of the conveyor in the inspection volume, the scatter spectrum of the conveyor materials is measured and stored in a reference database. When the scatter spectrum of the inspection region is detected and it is determined that the conveyor occupied a portion of the inspection region, the scatter spectrum is corrected by multiplying the conveyor material scatter spectrum by a weighting factor to account for the size of the inspection volume occupied and that amount is subtracted from the measurement.

Similarly, when part of the inspection volume is filled with air, as in cases when suitcase walls are targeted by the inspection volume, it is known that the contribution of the air-filled portion of the inspection volume to the scatter signal is approximately zero, and therefore, substantially all of the scatter signal can be attributed to the material in the remainder of the inspection volume. By accounting for the air volume contribution, the characterization of the material in the remaining inspection volume is rendered more precise. Optical detectors, such as a plurality of light-curtains, can be positioned across and within the scanning system to generate control signals that convey information about the height and edges of the container relative to the conveyor system and relative to the inspection region. It therefore can be calculated which portion of the inspection region is filled with air.

In another embodiment, transmission values for the scatter beam are measured by an array detector. An exemplary array comprises 16 channels and yields transmission data for 16 subdivisions within the inspection volume. The transmission values can be used to characterize the material distribution in the inspection volume. Based on these transmission values, approximate mass values can be determined for masses contained in each of the 16 subdivisions. For example, where the transmission detector value returns a value indicating the subdivision has material with zero thickness, it can be assumed that the subdivision is occupied by air.

In a preferred embodiment, the inspection volume is subdivided. By reducing the size of the inspection region, one can ensure that fewer differing materials occupy the same region and can therefore avoid the complex composite signals that get generated when multiple materials fill a single inspection region. In one embodiment, system resolution is increased by providing multiple energy dispersive detectors, such as 2, 3, 4, 5, 6 or more, in place of a single energy dispersive detector as shown in FIG. 4.

Figure 7:
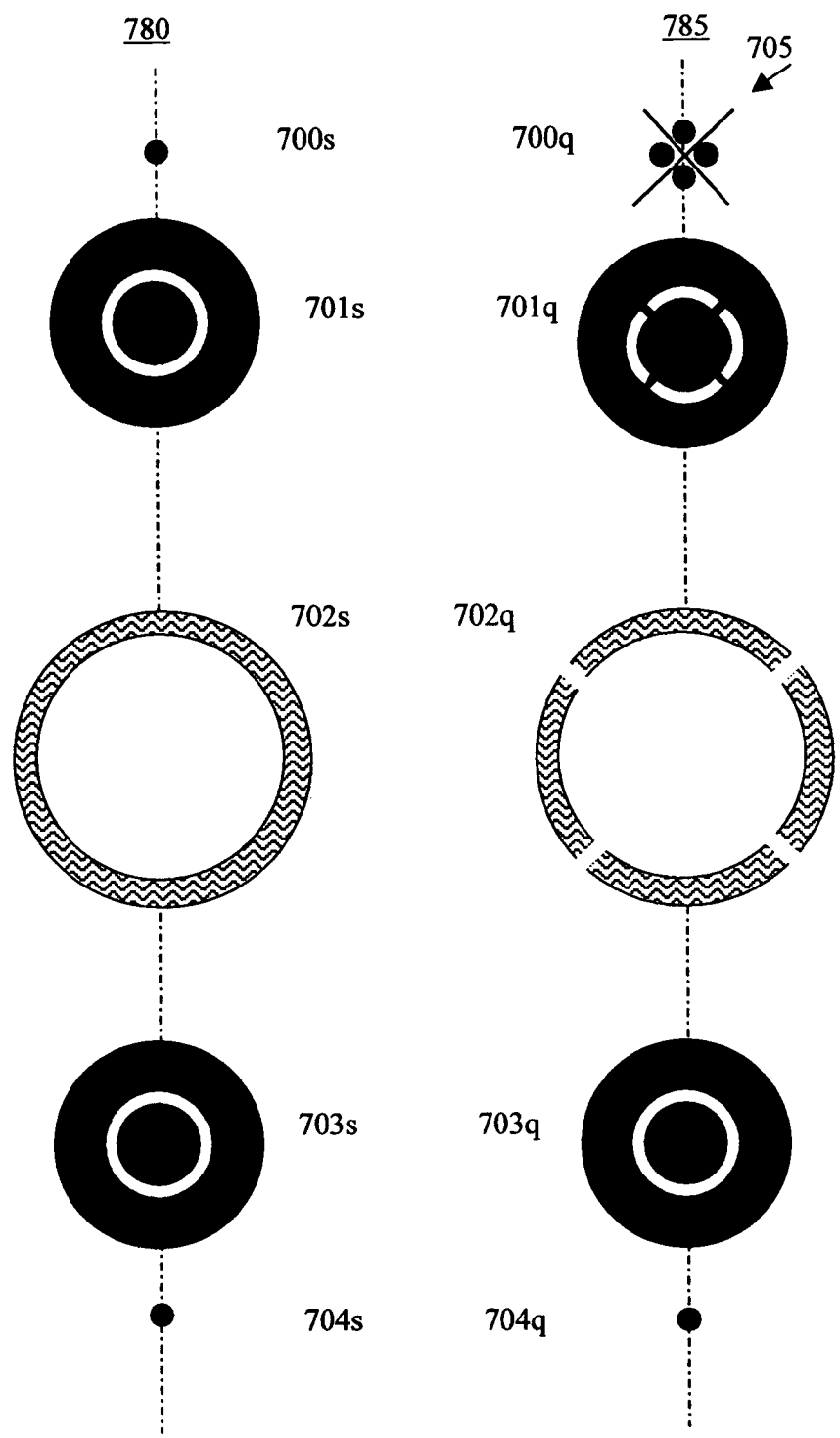
FIG. 7 is a schematic representation of a beam delivery system having multiple energy dispersive detectors.

Referring to FIG. 7, a schematic representation of the beam delivery system of FIG. 4 780 is shown relative to a beam delivery system having multiple energy dispersive detectors 785. A first system 780 comprises single detector 700s, circular aperture 701s, inspection volume 702s, circular aperture 703s, and X-ray focus 704s. The dark areas represent the presence of radiation blocking material, e.g. ¼ inch lead alloy, and the white areas represent areas that are transparent to X-rays above 30 keV. A second system 785 comprises an X-ray focus 704q, circular aperture 703q, divided inspection volume 702q, detector side beam shaping aperture 701q, and quadruple detector 700q. The aperture 701q is center-symmetric and consists of four slits, each conforming to part of a circle. The centers of the circular slits are chosen to be of the same pattern as the detectors of the quadruple detector 700q. For example, if the detector cluster consists of four channels centered on the four corners of a 2 by 2 mm square, the centers of the partial and circular apertures lay on a circle with diameter equal to the square root of 2 times 2 mm. The resulting inspection region for each individual detection region is about one quarter of the full inspection volume. A subdivided inspection region provides a higher spatial resolution of the second stage inspection. Clusters of energy dispersive detectors with their supporting electronics are commercially available from companies such as eV Products, Saxonburg, Pa.

If more than one scatter detector is being employed, a collimating system of vanes can be placed in front of the detector cluster orthogonal to the surface of the detector and in line with the plane of separation between each detector. Using a separator 705, diffracted radiation is more effectively limited to reach the appropriate channel in the cluster and, consequently, detected signals are more readily associated with materials from specific areas within the inspection region. The separator 705 extends from the surface of the detector cluster toward the surface of the adjacent aperture. The number of separator vanes is dependent on the number of detectors. A typical vane material and thickness is lead alloy of 0.5 mm thickness.

f. Operational Process of the Preferred Embodiment

Figure 9:
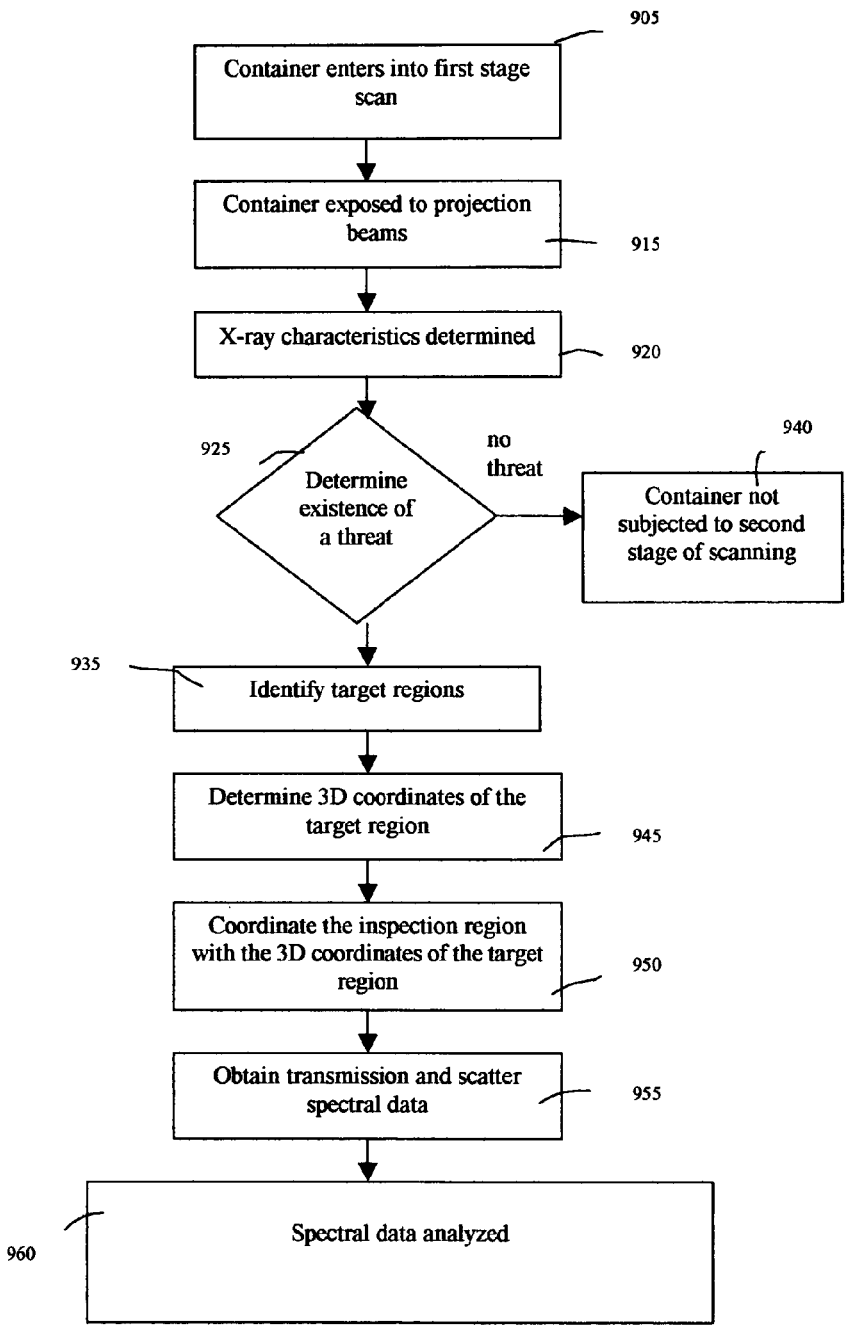
FIG. 9 is a flow diagram describing a plurality of steps for practicing one embodiment of the present invention.

Referring to FIG. 9, a flowchart summarizing the operational process of one embodiment of the present invention is provided. A container enters into the first stage scan 905 where it is exposed to a plurality of projected beams 915. From that exposure, X-ray characteristics are determined 920 and target regions containing potential threats are identified 925, 935. If no potential threats are identified, the container is not subjected to a second scanning stage 940. The three dimensional coordinates of the target region is determined 945 and, accordingly, the inspection region generated by the second stage scanning system is coordinated to coincide with the target region 950. The inspection region is subjected to X-ray radiation in order to obtain transmission and spectral data 955. The spectral data is then analyzed 960 to determine the existence of a threat. The data collected in the second stage scan comprises both localized dual energy transmission data and localized BRAGG diffraction spectra, which are subject to statistical variances, originating from photon signal fluctuations, partial volume limitations, or variations of the type of luggage and their contents, among other causes. As such, it is preferred to have a processing methodology that accounts for the fact that the raw data is not sufficiently sensitive to detect threats with sufficiently low false alarm rate.

In a preferred embodiment, the automatic threat resolution is performed by a probabilistic technique in which a plurality of input data points, obtained from the raw spectral scan data, contribute to the probability that the corresponding spectrum belongs to a particular class of threat or non-threat items. Such a probabilistic technique relies on the plurality of input data points as a whole rather than on individual data points. Although probabilistic classification techniques can include explicit, identifiable rules created by a programmer, the preferred techniques utilize a classification procedure that incorporates the results of training. For example, the classification algorithm can be used to process a training set consisting of patterns for structures of known classification. The results of this processing are used to adjust the algorithm, so that the classification accuracy improves as the algorithm learns by processing the training sets.

One type of trainable classifier that can be employed is an artificial neural network. Artificial neural networks attempt to model human biological neural networks to perform pattern recognition and data classification tasks. Neural networks are fine grain parallel processing architectures composed of non-linear processing units, known as neurons or nodes, which attempt to replicate the synaptic-dendritic interconnections found in the human brain.

Different types of neural networks exist. One type of network is a multi-player, feed-forward network. A feed forward network passes a signal by links from input nodes to output nodes, in one direction only. In most implementations, the nodes are organized into multiple layers: the input layer, output layer, and several "hidden layers" in between. The adjacent layers are normally fully interconnected.

Figure 8:
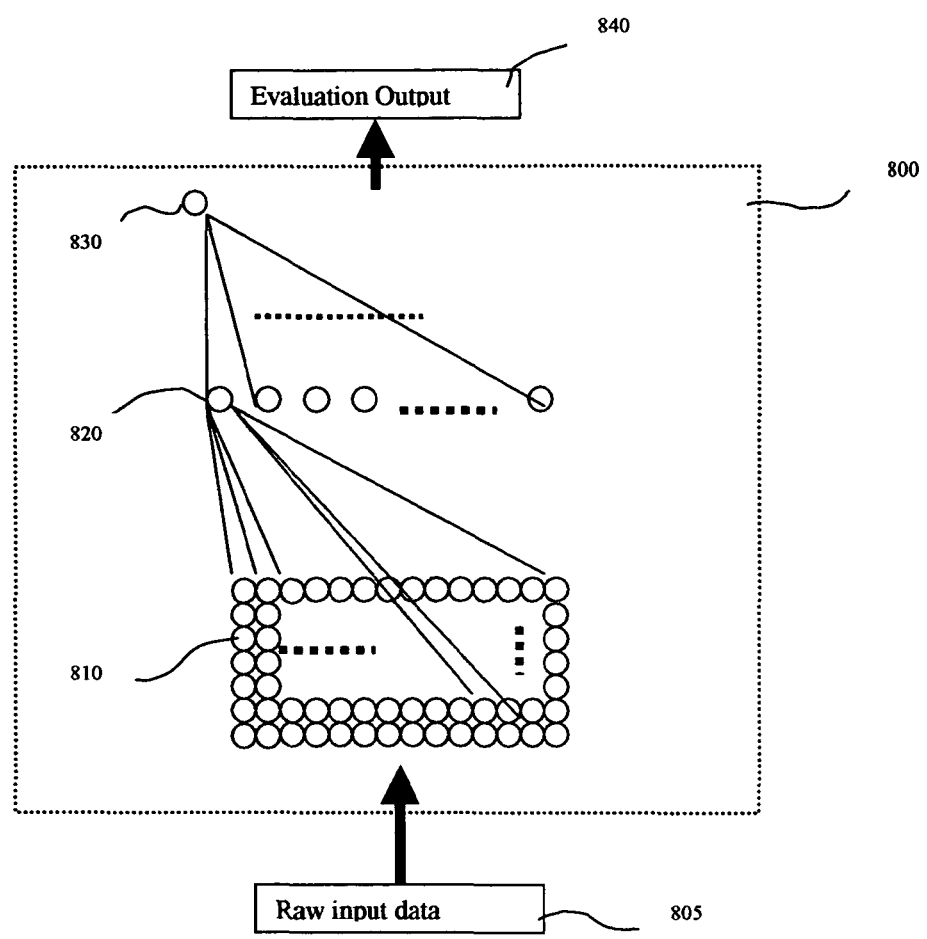
FIG. 8 is a graphical representation of an artificial neural network.

FIG. 8 depicts a schematic representation of a preferred type of artificial neural network 800 known as a hidden-layer feed-forward network consisting of an input layer 810 of neurons or nodes, at least one hidden layer 820, and an output layer 830. The neuron layers are linked via a set of synaptic interconnections. Each neuron in the input layer is typically connected to each neuron in the hidden layer, and each neuron in the hidden layer is typically connected to each neuron in the output layer, via a synaptic connection; these may be physical, electronic connections, or they may be embodied in software, as may be the neurons themselves, which software operates on conventional digital computers.

The neurons or nodes typically accept several inputs and create a weighted sum (a vector dot product). This sum is then tested against an activation rule (typically a threshold) and then processed through an output function. The output function could be a non-linear function such as a hard-limiter; a sigmoid function; a sine-function or any other suitable function known to a person of ordinary skill in the art. The threshold determines how high the input to that neuron must be in order to generate a positive output of that neuron. A neuron may be considered to be turned on, for instance, whenever its value is above a predetermined value such as, for instance, 0.9 and turned off with a value of less than another value such as 0.1, and has an undefined "maybe" state between those values. The connectivity pattern defines which node receives the output value of a previous node as their input. The connection between two neurons is realized in mathematical terms by multiplying the output of the lower level neuron by the strength of that connection (weight). At each instant of propagation, the values for the inputs define an activity state. The initial activity state is defined upon presentation of the inputs to the network.

The output response of any hidden layer neuron ($o_j$) and any output layer neuron is a function of the network input to that neuron defined by the difference of that neuron's threshold ($\theta$) and the input to it. The value of the input into each hidden or output layer neuron is weighted with the weight currently stored for the connection strengths between each of the input and hidden layer neurons, and the hidden and output layer neurons, respectively. Summing over all connections into a particular neuron and subtracting this sum from the threshold value may be performed according to the following sigmoid-type Fermi function:

$$o_j = [1 + \exp(\theta_j - \Sigma_i w_{ji} * o_i)]^{-1}$$

where i and j represent neurons of two different layers with j representing the higher layer; $\theta_j$ represents the bias value for j layer neuron; and $w_{ji}$ represents the strength of the connection between neuron i and neuron j. Alternatively, sine-type functions, or any other suitable function known in the art, may be used to obtain the desired type of response function for the output of a neuron. The weights are chosen so as to minimize the error between the produced result and the correct result. A learning rule defines how to choose the weight values. Several commonly used learning rules are back-propagation, competitive learning, adaptive resonance, and self-organization.

In a preferred embodiment, the artificial neural network uses back-propagation learning. The back-propagation learning algorithm, derived from the chain rule for partial derivatives, provides a gradient descent learning method in the space of weights and can be further understood by reference to D. E. Rumelhart, et al., Parallel Distributed Processing, ch. 8, pp. 322-28 (MIT Press, 1986) and Haykin, Simon (1999), "Neural Networks", Prentice Hall, both of which are incorporated herein by reference.

Back-propagation learning involves a set of pairs of input and output vectors. The network uses an input vector to generate its own, or actual, output vector. The actual output vector is compared with a desired output, or target, vector that may be defined usually in the course of training. The weights are changed to obtain a match between the target vector and the actual output vector. The conventional delta rule may be used for this calculation where the weight for a particular synapse or connection between units is adjusted proportionally to the product of an error signal, delta, available to the unit receiving input via the connection and the output of the unit sending a signal via the connection. If a unit is an output unit, the error signal is proportional to the difference between the actual and target value of the unit. If it is a hidden layer, it is determined recursively in terms of the error signals of the units to which it directly connects and the weights of those connections.

Thus, the training of a neural network is the process of setting the connection weights so that the network produces a desired output in response to any input that is normal for the situation. A supervised training refers to the kind of training that requires a training set, i.e. a set of input-output patterns. The back-propagation algorithm is an efficient technique to train a feed-forward network. It operates to send an error back through the network during the training process, thereby adjusting all the link weights in correspondence with their contribution to the error. The weights of the network therefore gradually drift to a better set of values. The initial weights are chosen randomly within reasonable limits and adjustments are left to the training process.

Referring back to FIG. 8, the artificial neural network 800 is trained on a suitably large set of threat and non-threat X-ray raw scan data, to generate an output 840, in accordance with the error back-propagation learning method described above. As described earlier, the required set of threat and non-threat raw scan data for training can be obtained either from the scanning system of the first stage or the scanning system of the second stage or both depending upon whether artificial neural networks are used to process scan data from the first stage or the second stage or from both the stages. Thus, the 'scan data' 805 to be used to train the neural net 800 may comprise of raw attenuation data, raw transmission photon counts, raw diffraction photon spectra or any other data known to a person of ordinary skill in the art.

The purpose of the neural network processing step is to have a processing means capable of recognizing a threat signature. A threat signature is defined as a spectrum, i.e. an array of numbers corresponding, on a one-to-one basis, to the discretized values of a physical quantity, such as the energy of X-rays, and includes unrelated, but relevant, other values, such as transmission detector array data, bag height, and other environmental factors. Although the spectrum may consist of any amount of data points, the present invention preferably operates on a spectrum data set of between 200 and 800 points and, more preferably, of approximately 500 points. Additionally, while the network may consist of any number of layers, it is preferred that it consists of four layers, including one input layer, two hidden layers, and one output layer. Further, while the network can have multiple output nodes with various indicators, it is preferred that, for the present invention, the network comprise a single node the output of which may be interpreted as either "yes, a threat has been recognized" or "no, a threat has not been recognized".

In a preferred embodiment, the raw diffraction spectrum data from the second stage is used to generate the required set of threat and non-threat scan data for training. These spectral counts represent raw, that is non-normalized, scan data 805 that is subsequently used to train the neural network 800. Alternatively, this scan data 805 may be further processed to generate a plurality of normalized data.

The scanning process is repeated to obtain scan data of a sufficiently large number of containers containing threat and non-threat items packaged in a variety of permutations and combinations to model real-world scenarios. This raw scan data, referred to hereinafter as training data, comprise an input-set to be used for training the neural network. Since the training data is obtained by scanning containers containing known materials, each output training data maybe further tagged to identify whether the respective training data represents a defined/known threat or non-threat item. This output training data maybe further stored in a suitable library or database such as a file server on a digital computer system along with the tagged identification information. Furthermore, the library or database of training data may be enhanced to incorporate and reflect all previously known threat materials and their corresponding raw 'scan data'.

In a preferred embodiment, two libraries are generated. A first library has signatures of threats. A larger second library has signatures of innocuous, or non-threat, items. The training process utilizes the threat and non-threat signatures to introduce into the system threat-like and non-threat-like signatures.

A threat-like signature is a linear combination of a sample from the threat library with a plurality of samples, such as two, from the non-threat library. The coefficients of the mix are randomly simulated. A simulated white noise is also added to the generated mixture, with its amplitude also randomly generated, within an interval from zero to a given fraction of the signal. A non-threat-like signature is a mixture of a plurality of non-threat signatures, such as two or three. The coefficients of the mix are randomly simulated. A simulated white noise is also added to the generated mixture, with its amplitude also randomly generated, within an interval from zero to a given fraction of the signal. Using signature mixes, incorporated with noise, the system is trained to recognize a threat or a non-threat by outputting an appropriate recognition answer from the last output node within the context of a reasonable level of noise and interference from overlapping items.

Figure 10:
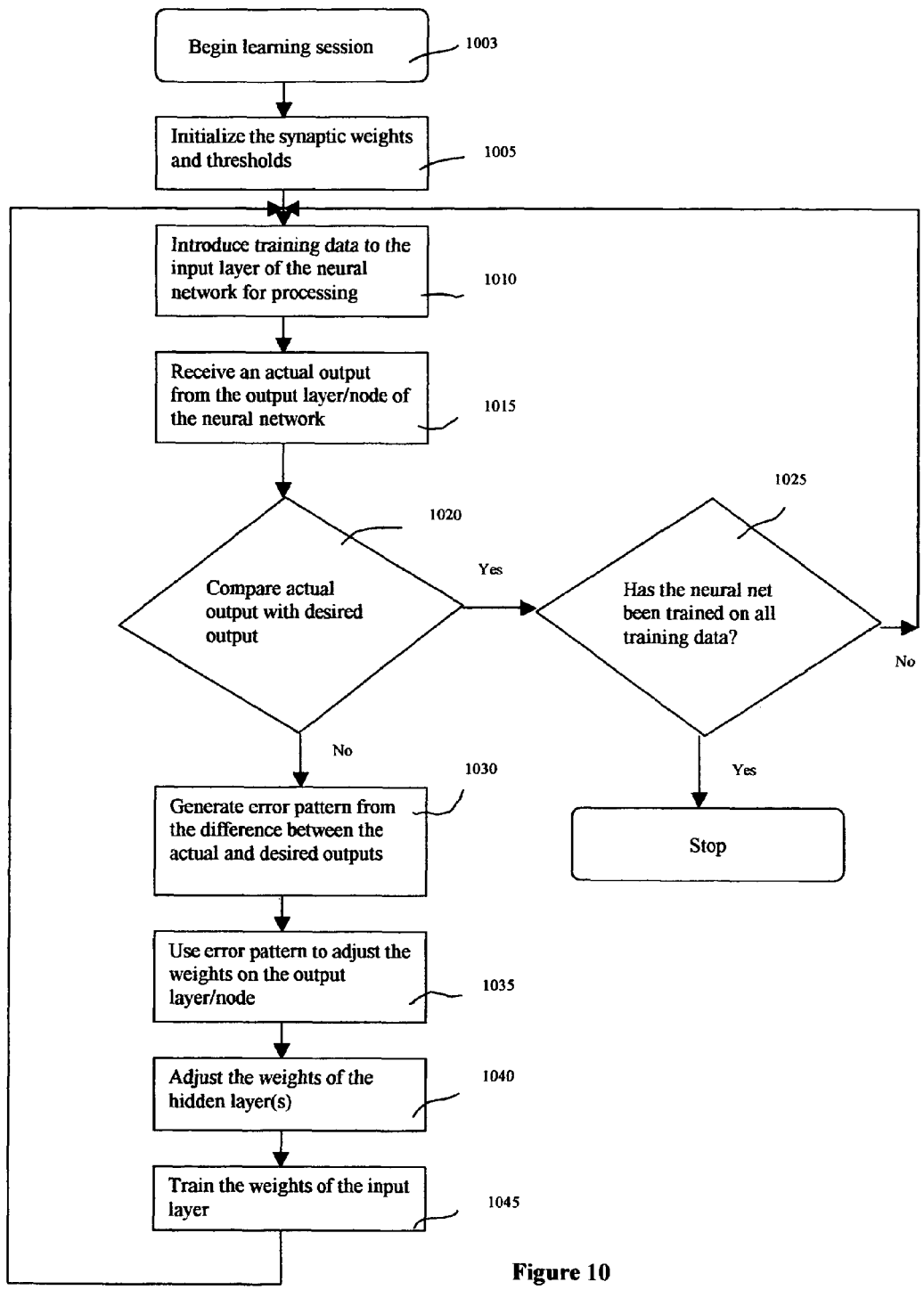
FIG. 10 is a flowchart depicting a process of training the neural network.

FIG. 10 depicts a plurality of steps, in flow diagram format, of one embodiment of the back-propagation training process of the invention. One of ordinary skill in the art would appreciate that the processing is conducted using a computer having a plurality of processors for executing the analytical processes described herein, embodied in at least one software program, a plurality of storage devices for storing the requisite data, library information, and other information necessary to conduct these analyses, and an output device, such as monitor, among other commonly known computing devices and peripherals.

At the beginning of the training process 1003, the synaptic weights and thresholds of the neural net are initialized 1005 with, for example, random numbers. After initialization 1005, the input layer of the neural network is introduced 1010 to a first set of training data and the net is run to receive 1015 an actual output. The neural net makes use of the randomly assigned weights and thresholds to generate an output on the basis of a suitable resolving function such as a sigmoid-type Fermi equation (described earlier), a sine function or any other function known to a person of ordinary skill in the art. The output could be in the form of differentiable signals such as numerals between, say, 0 and 1, in the form of positive or negative states implied by an output numeral of greater than or less than 0 respectively, or any other suitable indication as evident to a person of ordinary skill in the art.

The first set of training data is introduced into the system and, based on the random weights and thresholds, produces an output 'x', i.e. a numeral greater than 0. If the training data represents a threat, this output indication is set as a benchmark to identify a 'threat' while a numeral less than 0 maybe set to identify a 'non-threat' item. Once a suitable benchmark is set, the training process is repeated with the next set of training data and corresponding actual outputs are received. The actual output is compared 1020 with the desired output, defined by an operator with knowledge as to whether input data is or is not representative of a threat, for the corresponding set of training data that was fed to the neural net in step 1010. If the actual output received 1015 is commensurate with the desired or targeted output or, if the difference between the target and actual output falls below a predefined acceptable level, a check 1025 is made to see if the neural net has been trained on the entire set of training data. If not then the next set of training data is introduced to the neural net and the foregoing steps are repeated. The training process continues until the neural net has been trained on the entire set of training data.

If the comparison 1020 suggests that the actual output is not in agreement with the desired or targeted output, the ensuing additional steps are performed. The difference between the actual and desired outputs is used to generate 1030 an error pattern in accordance with a suitable back-propagation rule such as the 'delta rule' or any other error estimation rule known to a person of ordinary skill in the art. The error pattern is used to adjust 1035 the synaptic weights on the output layer such that the error pattern would be reduced the next time if the same set of training data were presented as the inputs. Then the weights of the hidden layers, preceding the output layer, are modified 1040 by comparing what outputs they actually produce with the results of neurons/nodes in the output layer to form an error pattern for the hidden layer.

The error can thus be propagated as far back over as many hidden layers as constituting the neural network. Finally, the weights for the input layer are similarly educated 1045, and the next set of training data is introduced to the neural network to iterate through the learning cycle again. The neural network is therefore trained by presenting each set of training data in turn at the inputs and propagating forwards and backwards, followed by the next input data, and repeating this cycle a sufficient number of times such that the neural network keeps getting closer and closer to the required weight values each time. Thus, the network, through the iterative back-propagation process, establishes a set of weights and thresholds for neural connections so that a desired output pattern is produced for the presented input information. The learned information of a neural network is contained in the values of the set of weights and thresholds.

In exemplary embodiments, the neural network is structured such that, through iterative forward and backward propagation, every node in a layer can be made to contribute to every node in a subsequent layer, only certain nodes in a layer maybe used to contribute to certain nodes in a subsequent layer, or every node in a layer contributes to every node in a subsequent layer but the impact of certain first layer nodes on subsequent layers are weighted relative to other first layer nodes. In a preferred embodiment, the nodes closest to subsequent layer nodes are weighted relative to other nodes in that same layer.

More preferably, links between the input layer and the first hidden layer are not chosen randomly, but selected to have a special distribution. Each hidden layer node is responsible for a region of the spectrum. Links to each hidden layer node from this region have higher weights. Therefore, the farther an input node is from this region, and the less responsible it is, the weaker the link with that input node. Together, the hidden nodes encompass the entire input layer spectrum. By distributing a pre-assigned degree of influence over links, a form of convolution is provided. This embodiment is particularly preferred where preprocessing is not reasonably effectuated because the input data size is too large.

Because new threats may develop over time, it is desirable to have a simple procedure that updates the network to recognize such additional threats. In a preferred embodiment, multiple networks are formed and trained to identify distinct threats. Therefore, new threat recognition is done by implementing a neural network as a set of multiple networks, each trained to identify a specific threat.

Each network group is formed and trained to address and recognize one threat. Thus, there is a one-to-one correspondence between the threats ($T_1, T_2, T_3 \ldots T_n$) and the groups ($G_1, G_2, G_3 \ldots G_n$). Network group $G_n$ is trained to recognize threat $T_n$. Where $G_n$ recognizes any other threat, $T_{n-2}, T_{n-1}, T_{n+1}$, it is not considered relevant. $G_n$ is trained using threat signatures of $T_n$ and a corresponding library of non-threat signatures. A group consists of a plurality, such as two, three, or four, completely separate networks, each similarly trained to recognize the same threat. Threat recognition is achieved where the average of the recognition results of each network indicates a threat. Where an additional threat is identified, $T_{new}$, a new group of networks, $G_{new}$, can be created, without having to retrain or modify all existing groups. This permits the more efficient, incremental addition of new threat recognition networks.

One of ordinary skill in the art would appreciate that the output of these network groups can be handled in various ways. Specifically, a system can output a threat alarm if the recognition result, averaged over all network groups, indicates a threat. A system can output a threat alarm if only one group of networks indicates a threat or if a subset of network groups indicates a threat. In a preferred embodiment, threat recognition is effectuated by monitoring the output of substantially all groups of networks. If the recognition result, averaged over all groups, indicates the existence of a threat, the output results of individual network groups are analyzed. If at least two groups indicate the presence of a threat, then the groups are reviewed to determine which threat has been recognized. One of ordinary skill in the art would appreciate that various derivations of the above-described process can be conducted without departing from the scope of this invention. For example, the threshold analysis can be performed even if only a portion of all network groups is monitored and the secondary analysis can be performed if fewer than two groups indicate a threat.

It is further preferred to regulate the balance between the sensitivity of detection with the selectivity of detection by incorporating an additional input node that is used to inject a sensitivity level into the training process. Systems with higher sensitivity will detect more threats at the expense of having greater false alarms. Systems with higher selectivity will have fewer false alarms, with the disadvantage of possibly not detecting all threats. In the course of operation, it may be necessary to change the sensitivity/selectivity balance, depending on various circumstances, and therefore it is desirable to have a means for doing so.

In one embodiment, a plurality of different networks is stored in a storage device in data communication with processors responsible for executing neural network analytical processes. Each set of networks has a different level of sensitivity, i.e. least sensitive, less sensitive, normal sensitivity, more sensitive, most sensitive. Depending on the requisite level of security (versus requisite level of throughput), the appropriate network set is loaded into the system. Alternatively, a network set having a standard level of sensitivity may be used in operation and a parallel network set, having varying levels of sensitivity, may be concurrently loaded and ready for use, when necessary. Having a parallel network avoids downtime associated with loading new network sets into local memory, or RAM.

Networks having varying degrees of sensitivity are developed by incorporating a sensitivity variable in the training process. With each recognition task, a desired level of sensitivity is communicated to an additional input layer node, thereby inherently incorporating it into the training process. Every training event could further be associated with a randomly selected sensitivity level, selected from within a reasonable range. Training is therefore conducted with the selected level of sensitivity.

The embodiment of back-propagation learning process, as described with reference to the flow diagram of FIG. 10, assumes that the training data is first collected by operating the first and/or second scanning systems offline, namely by scanning a large number of baggage containing known threat materials camouflaged amongst non-threat items in a variety of combinations to represent a variety of concealment scenarios. The training data so obtained is then used to educate the neural network that can then be used to operate in real-world situations. Thus, in this embodiment, when the first and/or second stage systems are online, that is operational at real-world sites such as at airports for luggage inspection, the associated neural network is already partially educated (on the training data obtained through test baggage) to discern threat from non-threat items.

However, in another embodiment of the back-propagation learning process, the neural network need not be taught through the scanning of test baggage prior to running the first and/or second scanning systems online. Instead the first and/or second scanning systems can be operated online and the scan data can then be fed into the neural network in real-time. On the basis of this real-time scan data, the neural net is made to classify threat and non-threat items. At the same time, the scanned image of the baggage is also presented to an operator in the form of a visual display such as on a conventional computer screen, as is known in the art. The operator compares the output of the neural net with his own observation of the scanned baggage. In case the output of the neural net is found to be erroneous, the operator prompts the neural net with the correct or desired output, enabling the neural network to adjust its weights and thresholds accordingly. Thus, in the second embodiment when the system is first used, it will have relatively little knowledge about threat and non-threat materials to be identified and recognized. However, with sufficient positive reinforcement of a relationship between the acquired scan data and operator prompted identification, the neural network will learn how to identify threat objects. This self-learning process enables the neural network to learn continuously.

The on-line, self-learning training process does have certain advantages. A company or organization that uses the present invention may not want to share or disclose data to third parties due to privacy or security reasons. Therefore, it may be essential to enable self-learning. Furthermore, the flow of data may change seasonally depending upon how containers change. Specifically, seasonal variations do occur in airline passenger travel where passenger bags may get larger in the winter to accommodate more clothing or the number of total bags may increase due to larger numbers of people traveling in the summer. To address such seasonal variation, it is more practical to allow on-line autonomous adaptation.

Finally, there may be a variety of system users in different geographical regions that experience different types of threat and non-threat items. In such cases, a standard library may not be as helpful as self-taught systems that automatically learn in accordance with its own unique context. More specifically, over time, a system in the field will be trained on containers that have threat and non-threat items unique to their geographic context. Due to operator training and interaction, a particular system would therefore develop a trained processing system tailored to their geographical context. It is preferred, however, that, irrespective of the geographical location, systems get periodically trained using threats that are new or infrequently seen to ensure that the system does not forget the identity of such threats. This update could be performed by the statistically controlled re-injection of threats from existing threat databases.

Although this online self-learning process has been described separately as an embodiment, this continuous self-learning process can be used in conjunction or combination with the offline teaching process of the first embodiment, using test baggage. In a preferred embodiment, the neural network is first trained on scan data obtained by running the X-ray system offline on test baggage and then through operator prompts in real-time operations as well, so that the ability of the neural net, in identifying objects, continuously improves through self-learning. Nevertheless, the system may undergo retraining offline using data from multiple site locations, thereby taking full advantage of the sum total of learning being generated by the operation of multiple systems.

Operationally, acquired scan data is fed into the neural network for identification. If the object is identified with a high degree of confidence, the identification and scan image is conveyed to an operator, along with an indication of what the object may be, to enable the operator to take an action, including conducting a hand search, questioning the container owner, permitting the container to pass, or calling in additional personnel. In one embodiment, the operator provides feedback to the system based upon the identity of the threat/non-threat and action taken. For example, if the system identifies the existence of a threat, the operator can check the container to determine if a threat exists and then inform the system whether it was or was not correct. If correct, the neural network increases its confidence factor for that object's scan data and stores the scan data in a suitable database as an exemplar for retraining. If incorrect, the neural network implements the error back-propagation process to suitably adjust its weights and thresholds and stores the scan data in a suitable database as an exemplar for retraining.

This on-line adaptation process using incoming data requires certain precautions, however. It is preferred that the system utilizes groups of networks, which are accompanied by libraries of threat patterns and innocuous patterns, and that the system is not authorized to modify these libraries. It is further preferred to include an additional library, a buffer-library, that is available for modification based upon incoming data. Specifically, the buffer library comprises incoming new data, and is preferably periodically cleansed of older data. Consequently, the networks are being re-trained using the buffer-library and the two stable libraries, with a proper adaptation time scale. Several previous versions of network groups are stored as a back up and a comparison of newly adapted system with its older versions can be conducted and produced in the form of a report. As described, on-site training can be set up as an automatic feature, but operator input may be required in the rare case of a real alarm.

IV. Alternate First Stage and/or Second Stage Systems a. Nuclear Quadrupole Resonance (NQR) Employed as a First or Second Stage Scanning System In addition to the technologies disclosed above, other technologies could be incorporated with the scanning system of the present invention. The invention as described here may be applied to a dual-stage system and method or, in the alternative, the processing techniques discussed herein can be applied to each of the individual scanning stages. Co-pending U.S. patent application Ser. No. 10/751,563, filed on Jan. 5, 2004 and titled, "NQR Based Inspection System Using A Highly Resonant and Compact Magnetic Structure" is herein incorporated by reference in its entirety, and discloses a compact resonator probe that can be placed in proximity to shielding devices, additional resonators probes, and other components of an article screening system. Also disclosed is a resonator probe in which the number of relays or mechanical actuators employed is reduced or eliminated, thereby solving many of the problems encountered in the prior art.

NQR is a magnetic resonance technique, closely related to Nuclear Magnetic Resonance (NMR), suitable for detection and/or analysis of bulk materials that contain a quadrupolar nucleus. Examples of such materials are nitrogen-containing explosives such as RDX, TNT and PETN and chlorine-containing narcotics such as heroin and cocaine. Atomic nuclei with a spin quantum number of greater than ½ and having non-spherical electric charge distributions possess electric quadrupole moments. Quadrupole resonance arises from the interaction of the nuclear quadrupole moment of the nucleus with the local applied electric field gradients produced by the surrounding atomic environment. NQR analysis for a given material involves the irradiation of a sample that has been placed in a test volume with a pulsed RF magnetic field. The frequency of the applied field used must be at or very close to one of the nuclear quadrupole resonance lines of the material under analysis. These frequencies are unique to individual materials and therefore allow for very specific identification of a material under analysis.

The exemplary NQR system, as used in either the first stage or second stage of the present invention, employs a vane-tuned enclosed resonator coil design which is more compact, less susceptible to receive or generate radio frequency interference, has a low manufacturing cost, has reduced flux leakage and can be placed close to other resonator probes of similar design and sensing equipments.

Referring back to FIG. 1, as described with reference to the embodiment described above, a dual stage scanning system 100 comprises a housing 130, which encompasses a conveyor system 115 for moving containers, baggage, luggage, or similar object 110 through a plurality of scanning stages 150, 155. The NQR system, as described below, may be in either stage 150 or stage 155 of the dual stage scanning system. A sensor system 165 is connected at the entrance to determine when an object being scanned 110 enters the scan field and communicates with a controller [not shown] to activate or deactivate an X-ray radiation source, 170, 172, as needed. A lead lined tunnel 180 surrounds the conveyor to reduce radiation leakage outside the equipment. At least one radiation source is not expressly depicted in FIG. 1 and would be visible if the system were viewed from the opposite side.

Figure 11C:
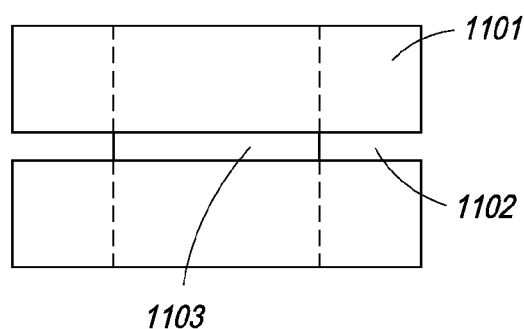

The NQR system that may be employed in the dual stage scanning system will now be described in details with reference to the Figures. FIGS. 11(a), 11(b), 11(c) and 11(d) show the front view, side view, top view, and isometric or perspective view of the resonator probe body, respectively. Referring to FIG. 11(a), the probe or basic resonator has a rectangular or cubic volume, referred to generally as a box-like structure 1101, and is made from a conductive material. In one preferred embodiment of the invention, this conductive material is a metal due to its relatively low resistivity. More specifically the metal will be one of lower resistivity such as, but not limited to, silver, copper or aluminum. Copper is a preferred choice due to its high conductivity and relatively low cost. The box-like structure 1101 is configured as an enclosed resonator probe, preferably with rectangular, orthogonal edges for manufacturing ease.

Figure 11D:
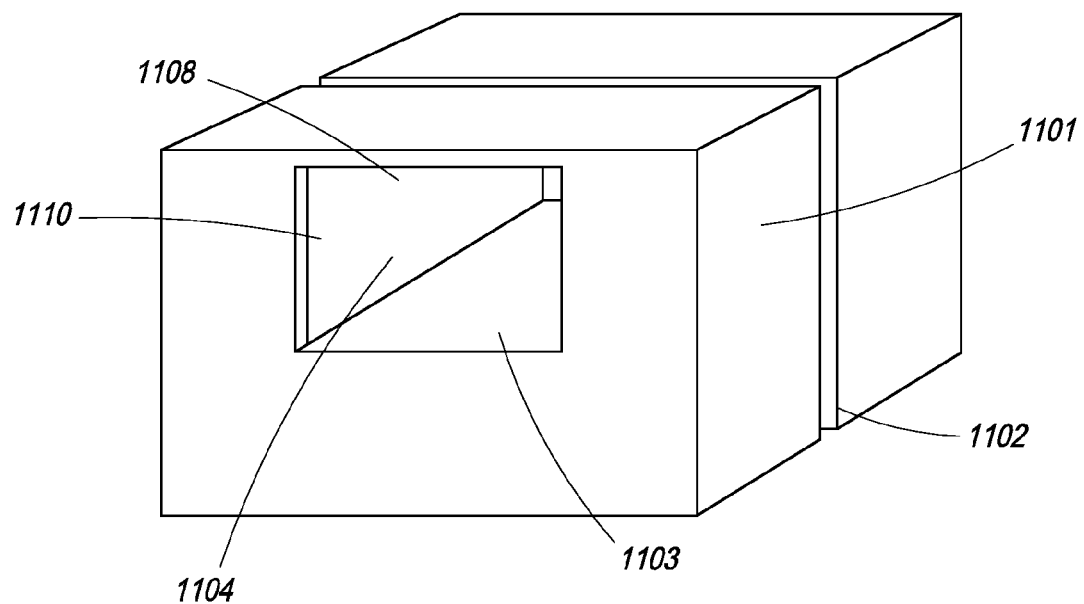
FIG. 11(d) depicts a perspective view of the resonator body of the NQR security system in FIGS. 11(a), 11(b), and 11(c)

Referring to FIGS. 11(b) and 11(c), the box-like structure 1101 has a continuous split 1102 around the outside perimeter. The front side and back side of the box-like structure 1101 are joined together, internally at the middle of the structure, by a platform 1103 made from the same material as the box-like structure 1101. Referring to FIG. 11(d), the enclosed resonator probe 1101 has platform 1103, a top wall surface 1108 parallel to platform 1103, and two inner side walls 1110, which connect the inner top wall surface 1108 and platform 1103, forming a rectangular cutout or inspection volume 1104, through which samples to be analyzed are passed. It is preferred that the toroid of the present invention be rectangular and elongated rather than rounded and circular.

Figure 12A:
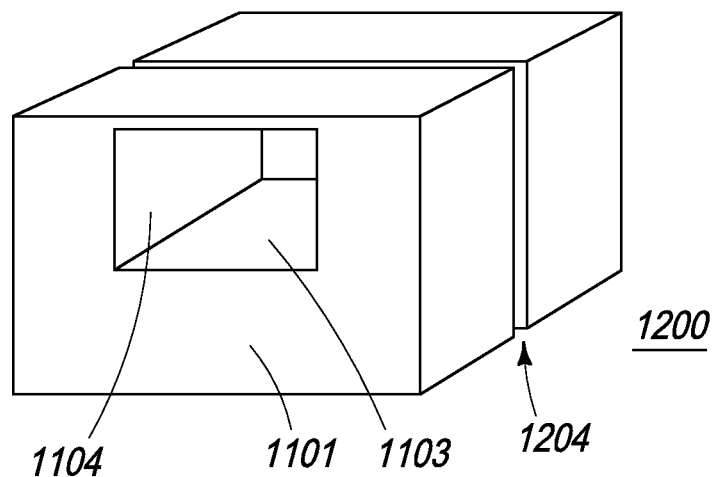
FIG. 12(a) illustrates the layout of an enclosed resonator probe in a preferred NQR security system as used in the present invention.

FIG. 12(a) shows the layout of enclosed resonator probe 1200. In one embodiment, enclosed resonator probe 1200 is essentially a single turn toroid fabricated, in a preferred embodiment, from copper sheets. The toroid of the present invention is fabricated from flat sheets of copper bent and soldered into position, creating orthogonal sides, which reduce its manufacturing cost. The tuning capacitors 1204 are provided in the probe body, distributed along the continuous split 1202 around the perimeter of probe 1200, and are electrically connected to the probe 1200 to form either a series or parallel resonant LC circuit. The resonator probe 1200 is therefore a highly resonant compact magnetic structure.

Figure 12B:
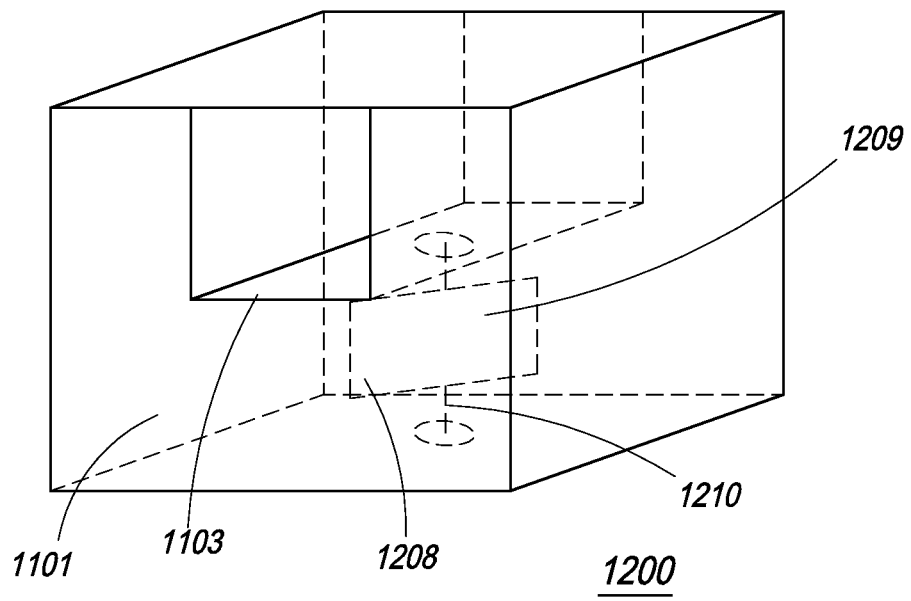
FIG. 12(b) is a drawing depicting the inspection volume or cutaway of the enclosed resonator probe in a preferred NQR security system as used in the present invention.

FIG. 12(b) depicts the inspection volume 1104 of the enclosed resonator probe 1200 showing tuning vane 1208 housed within the hollow central portion of enclosed resonator probe 1200 and below platform 1203. The tuning vane 1208 comprises a conductive plate or loop 1209 mounted on a pivot axle 1210 passing through the enclosed resonator probe 1200. The pivot axle may be rotated either manually or automatically via the control of a controller.

Figure 12C:
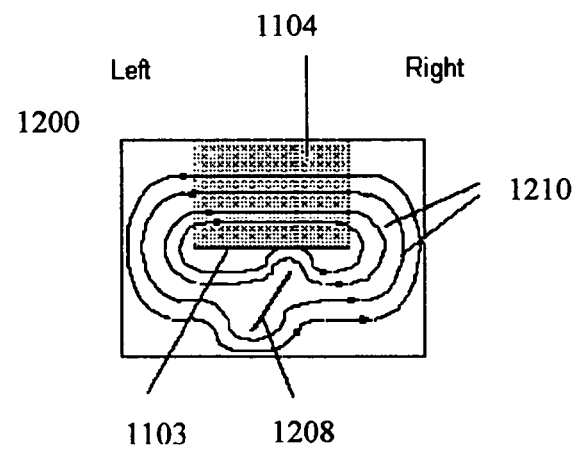
FIG. 12(c) is a drawing illustrating the coil cross-section and shows the magnetic flux path within the resonator body of the NQR system of the present invention.

The box-like structure 1101 provides the inductive component of a resonant circuit. It is the inductance of this box combined with the applied capacitance of tuning capacitors 1204 that determines the resonant frequency of the enclosed resonator probe 1200. Referring to FIG. 12(c), which depicts the enclosed resonator coil cross-section 1205, the parallel currents that flow within the resonator probe 1200 upon resonance pass from back to front across platform 1103 in the center and radiate across the front face of resonator probe 1200 outward from the platform 1103 towards the outer perimeter (this path is distorted in the area of the hole in the front face). The currents then flow from the front to the back of resonator probe 1200 across the outer walls of enclosed resonator probe 1200, subsequently passing across the distributed capacitor 1204.

The currents pass from the outer perimeter on the back face of the resonator probe 1200 towards the center of the back face to the platform 1103. This current path produces a magnetic flux path (or magnetic lines of force) 1210 around the inside of the resonator probe 1200 as shown in FIG. 12(c). The tuning capacitors 1204 distributed around the continuous split 1102 in the resonator probe body 1200 run parallel to the primary magnetic flux path 1210.

The multiple parallel current paths resulting from the design of resonator probe 1200 and distributed tuning capacitors 1204 enables the resonator probe 1200 to have a very low resistance, resulting in low resistive losses, and therefore a very high Quality (Q) factor. In addition, the design of the resonator probe 1200 in the present invention leads to its low susceptibility to transmitting and receiving radio frequency interference or noise, and reduced flux leakage. The resonator probe 1200 is an efficient magnetic structure with nearly all the magnetic flux generated by the system constrained within it, further allowing for a high Quality (Q) factor. A high Q factor is important in the effective performance of a resonator probe because the higher the resonator Q factor the higher the signal to noise ratio of any measurements made from test samples. A high Quality (Q) factor also leads to higher power efficiency.

Figure 12D:
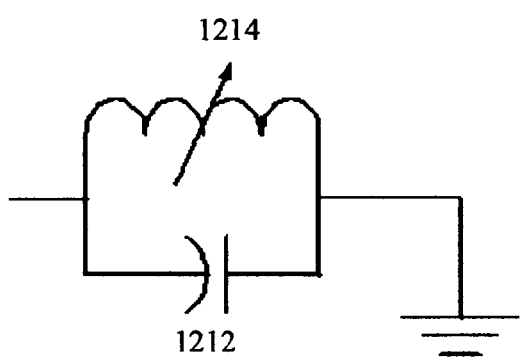
FIG. 12(d) depicts the equivalent circuit diagram of an enclosed resonator probe in a preferred NQR security system as used in the present invention.

The equivalent circuit diagram of the enclosed resonator probe 1200 is shown in FIG. 12(d). The resonant frequency of the enclosed resonator probe 1200 is changed by either altering the inductance 1214 of the resonator probe 1200 or the applied capacitance 1212 of the tuning capacitors 1204, described above. In both cases this can be done either continuously or discreetly depending on which methods are chosen.

The applied capacitance 1212 of the tuning capacitors 1204 is adjustable by use of either variable capacitors or switches which add or subtract capacitance. A preferred method is to use a variable angle conductive vane 1208 in the flux path within the resonator probe 1200 as shown in FIGS. 12(b) and 12(c). Changing the angle of vane 1208 effectively alters the cross-sectional area of a segment of the resonator probe 1200, interrupting the flux path 1210 within the resonator coil 1200 to a variable degree. This has the effect of changing the resonator's inductance 1214 and therefore, its resonant frequency. The closer the angle of the tuning vane 1208 to normal (90 degrees) with respect to the flux path 1210, the greater the area of flux path 1210 intersected, the lower the inductance 1214 and therefore the higher the resonator's 1200 tuned frequency. The angle of tuning vane 1208 can be changed in various directions provided that it is changing the amount of flux path 1210 that is intersected. This method allows fine-tuning of the resonant frequency of the resonator probe 1200. Alternatively, the inductance 1214 can be adjusted by switching different sized conductive loops, which block different amounts of flux 1210. Coarse adjustment of the resonant or tuning frequency of the resonator probe 1200 is best achieved by switching the resonant circuit's tuning capacitance 1212.

Figure 13:
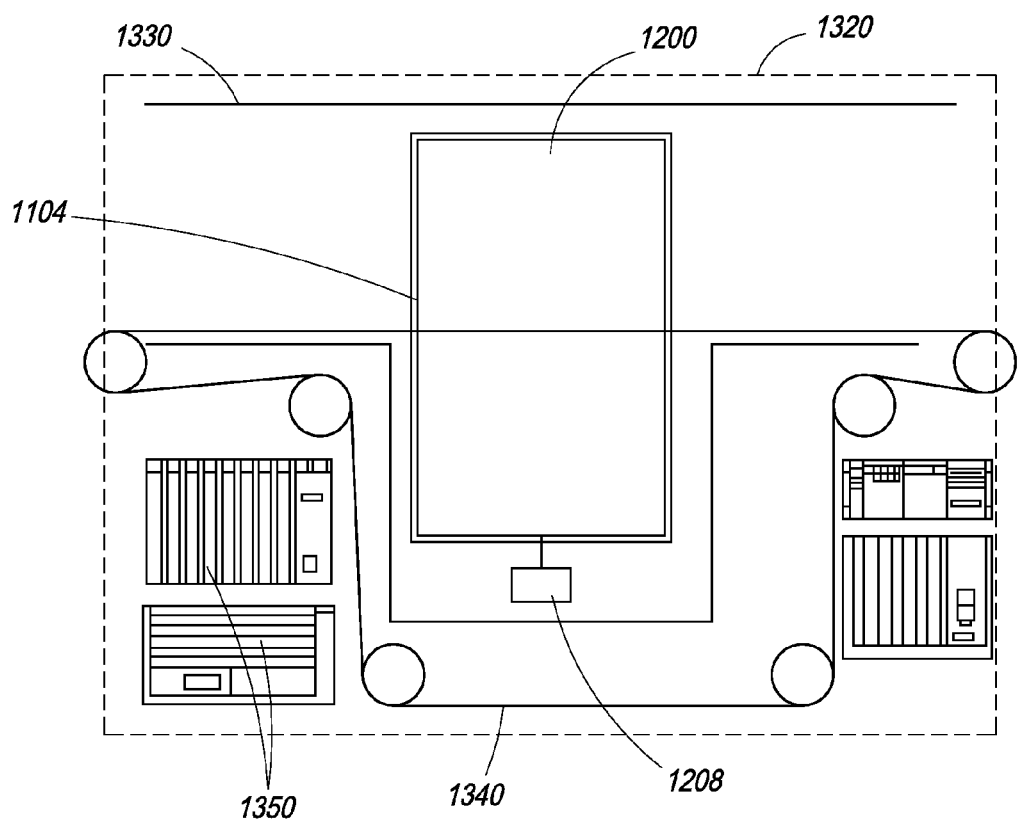
FIG. 13 is a drawing depicting the layout of a NQR baggage scanner having single resonator coil in another preferred embodiment of the NQR system of the present invention.

FIG. 13(a) illustrates the layout of an exemplary NQR baggage scanner as may be employed in the present invention as either a first or second stage to detect the presence of contraband within baggage. It is particularly effective in detecting contraband materials in configurations that are more difficult to detect using more established detection technologies since the result of an NQR scan of a material under analysis depends on the number of a specific quadrupolar nuclei present in the material, regardless of how those nuclei are distributed. The enclosed resonator probe 1200 preferably made from copper is placed within an outer electrically conductive electromagnetic shield (or RF shield) 1330, preferably made from, but not limited to aluminum. The electromagnetic shield 1330 reduces the effect of external magnetic fields and also helps to constrain the generated magnetic and electric fields within the resonator probe 1200. Thus the reliability of the analysis/detection is enhanced and resonator probe 1200 remains essentially immune to external electromagnetic (RF) radiation. The electromagnetic shield 1330 also protects the external electronic apparatus from picking up electromagnetic (RF) radiation generated by resonator probe 1200. The resonator probe 1200 is tuned at NQR frequencies of the target substance under detection or analysis. While the excitation frequency need not be exactly the same as the NQR frequency of the target substance, it is ideally within 500-1000 Hz. Tuning vane 1208 is used for fine-tuning of the resonator probe 1200.

A conveying means such as conveyor belt system 1340 is provided through the inspection volume 1104 in the resonator probe 1200 for transporting the luggage through the inspection volume 1104 of the scanner. The conveyor belt 1340 may be continually or incrementally moved via the control of a controller to pass a series of samples through the resonator probe 1200. The NQR scanner is preferably encased in its entirety in cosmetic outer panels 1320. The necessary electronic circuits 1350 are provided for generating RF pulses, measuring the NQR, detecting suspicious baggage, activating alarms, and tuning enclosed resonator probe 1200.

In another preferred embodiment of the preferred NQR system of the present invention, a plurality of resonator probes can be placed in proximity to each other within the same electromagnetic shield rather than using a single probe coil containing a number of components for tuning to different frequencies for detecting various types of contraband. Each of the resonator probes, in this particular embodiment, is tuned to a different NQR frequency. In most cases, the fine-tuning for each unit is enabled via a single fine-tuning mechanism, responsible for controlling the plurality of resonator probes.

Figure 14:
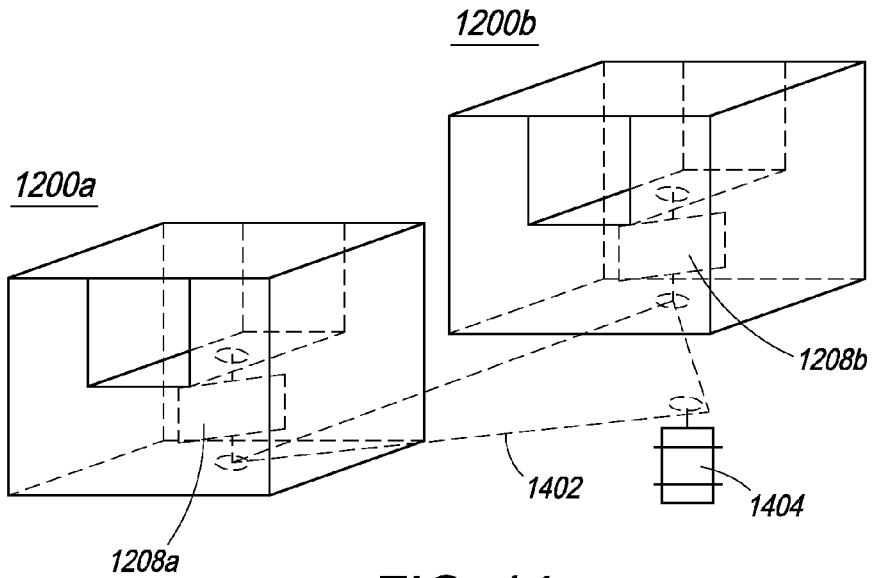
FIG. 14 is a diagram showing a single tuning mechanism for controlling tuning vanes of two or more resonator probes, in another preferred embodiment of the NQR system of the present invention.
Figure 15:
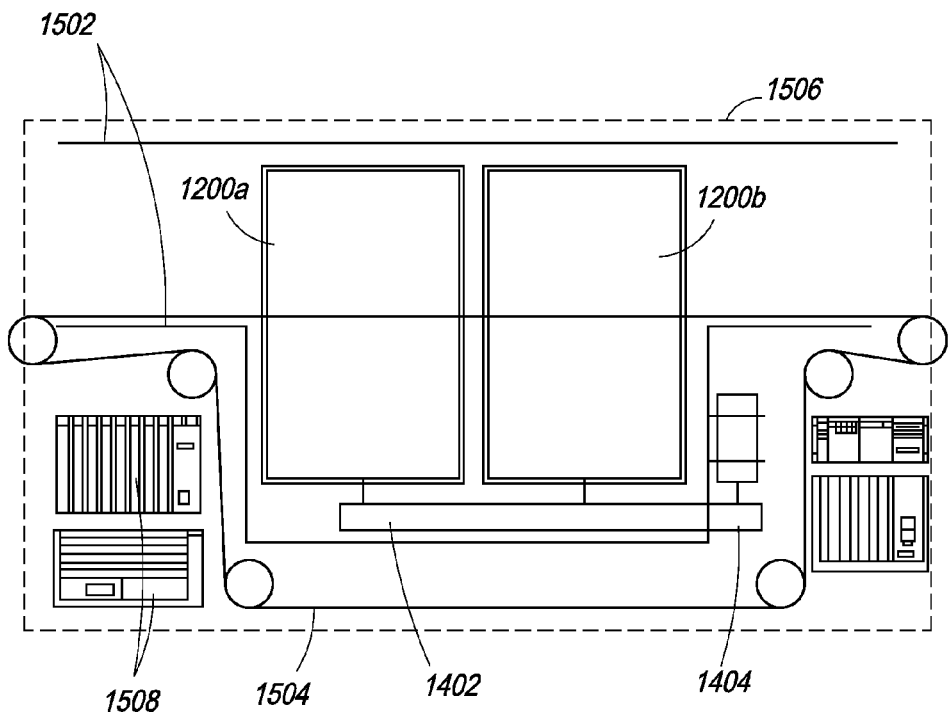
FIG. 15 is a diagram depicting the layout of a dual coil NQR baggage scanner with single tuning mechanism, in another preferred embodiment of the NQR system of the present invention.

FIGS. 14 and 15 depict how the resonant frequency for more than one resonator probe can be driven from the same motor 1404, which can in turn be driven from a single control system. This method of tuning multiple resonator probes can be extended from a minimum of two resonator probes to as many resonators probes as desired for a given system depending on the requirements for the system. A significant difference between this resonator probe configuration and other designs is the possibility of operating multiple resonator probes in close proximity with minimal mutual interference since most flux is constrained within the resonator coil itself.

Additionally, the nature of the resonator probe 1200 (strong magnetic fields generated on the inside and magnetic fields canceling on the outside), allows electromagnetic shielding to be placed in close proximity to the resonator probe 1200 without disrupting the magnetic fields generated inside the resonator probe. Furthermore, the design of resonator probe 1200 is such that it is less susceptible to electromagnetic interference, both generated and induced, thereby decreasing the need for electromagnetic shielding as compared to other probe designs.

The NQR security system of the present invention, as described herein, may be applied to a dual-stage scanning system and method as described above, or, in the alternative the processing techniques discussed herein can be applied to each of the individual scanning stages. Specifically, the NQR security system can be employed as one of a plurality of scanning stages with the other stages being of the types discussed herein, such as X-ray scatter or X-ray transmission. Alternative the NQR security system can be incorporated into a single stage with or without additional technologies, such as X-ray scatter or X-ray transmission. In addition to the technologies disclosed above, other technologies could be incorporated with the scanning system of the present invention.

b. An Exemplary Microwave Metal Detection and Imaging System

In another preferred embodiment, the present invention is directed toward a microwave metal detection and imaging system that uses multiple transmitter/receiver pairs (also referred to as transmit/receive pairs) of microwave antennas to measure the presence of conductive material appearing in the space between each transmit/receive pair. Each antenna pair has an ideal primary transmission path, which is effectively the shortest route between the two antennas. Conductive material will block or attenuate the transmission between the antenna pairs if it is placed in the direct transmission path (the space between each transmit/receive pair).

Transmit/receive pairs are arranged in a linear array. The object to be scanned passes through such transmit/receive pairs (for example, by means of a conveyor belt), creating a two-dimensional image of conductive items concealed within an object under inspection. By repeating this process for each dimension (in a three dimensional structure, the dimensions run along each of an x-axis, a y-axis, and a z-axis, whereby the conveyor belt runs along the x-axis and image patterns are obtained in the y and z-axes), it becomes possible to estimate the volume of conductive items/objects. An appropriate design of antenna rays enables the measurement of the metallic or conductive content of items concealed within a three-dimensional object, in each physical dimension, while the object under examination moves in only one direction (for example, along the x-axis, as on a conveyor belt).

The transmit/receive pairs are designed to prevent the multiple pairs in the array from interfering with one another. Furthermore, if the pairs are not appropriately designed, multiple microwave reflection paths are possible, which can result in confusing data being developed from transmission paths other than the most direct transmission path, i.e. between designated transmit/receive pairs. This problem is solved by a unique combination of the system layout, proper material selection, and antenna design.

Figure 16:
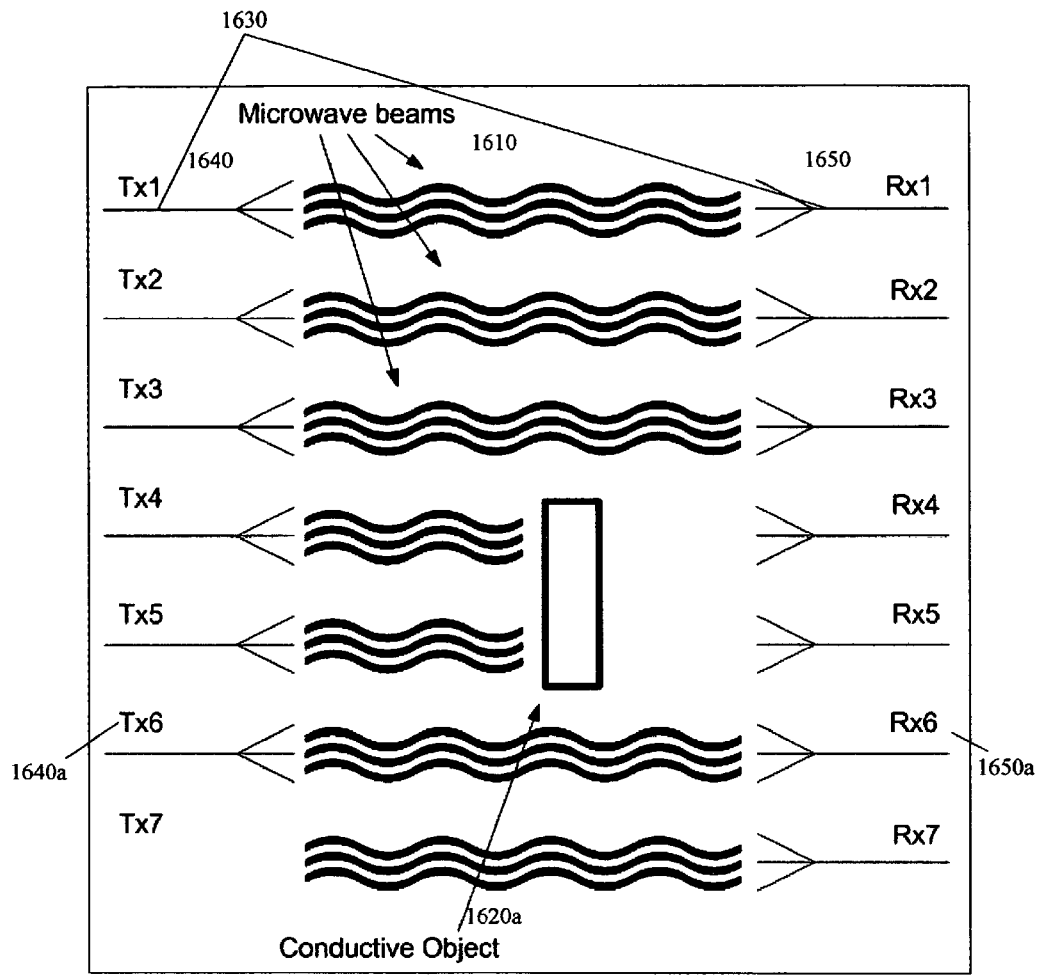
FIG. 16 illustrates pathways of transmit/receive pairs in one embodiment of a microwave imaging system of the present invention.

Referring now to FIG. 16, the most direct transmission pathways of transmit/receive pairs 1630 as in the present invention are depicted. Transmitter antenna 1640 and receiver antenna 1650 comprise transmit/receive pair 1630. In microwave imaging system 1600, microwaves transmit, to a large extent, directly from a transmitter antenna 1640 to its corresponding receiver antenna 1650 in a straight line path, thereby forming microwave beams 1610.

The microwave frequency and amplitude is selected in a suitable range to allow for discrimination of conductive and non-conductive items and such that transmission is possible through normal non-conductive luggage materials. The preferred amplitude of the transmitted signal is at significantly above the noise floor such that measurements are a clear indication of the presence of conductive/non-conductive items and are not determined by fluctuations in microwave noise. The frequency of operation is such that penetration is sufficient for the detection and imaging of objects within typical packages and bags yet with a minimal amount of inaccuracies introduced due to items with high dielectric loss. In one embodiment, the frequencies utilized are in the range of 1 to 30 GHz and, more particularly, in the range of 3-12 GHz. The amplitude should be sufficient to generate a signal to noise ratio of preferably at least 4 after traveling through normal, non-metallic clutter found in typical baggage.

Non-conductive materials should largely allow the microwaves to pass relatively un-attenuated. However, the introduction of a conductive object under inspection 1620 between the transmit/receive pair will substantially attenuate the transmission of microwaves. This is particularly true if conductive object 1620 is metallic.

c. Microwave Imaging as a Single Stage System

Figure 17:
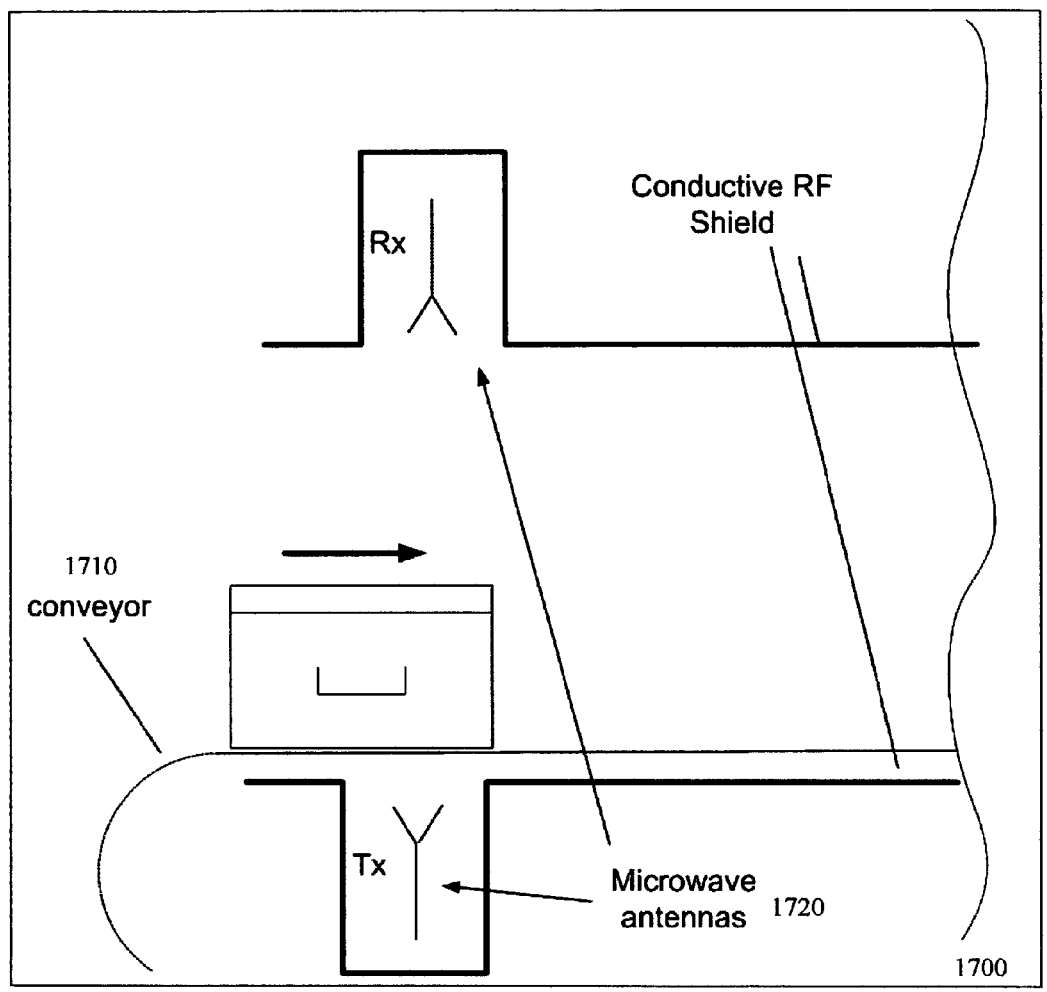
FIG. 17 depicts microwave antenna arrays housed in a system with a complimentary security technology, including, but not limited to an NQR shielding waveguide, X-ray tunnel, or CT tunnel.

In a preferred embodiment of the present invention, the object under inspection is passed through a conveyor belt system 1700, as shown in FIG. 17. FIG. 17 is an exemplary imaging system that would use conveyor belt 1710 to progress the object under inspection through one or more transmit/receive pairs of microwave antenna array(s) 1720. As conveyor belt 1710 passes an object under inspection through the one or more microwave antenna array(s) 1720, a record of the attenuation between each transmit/receive pair within microwave antenna array(s) 1720 is kept for varying positions of conveyor belt 1710. The record is directly related to the contents of the object under inspection and an image of attenuation levels observed within the object under inspection can be displayed.

To keep the transmission path between distinct transmitter receiver antenna pairs separate and to prevent cross talk between channels, each transmit/receive antenna pair could be frequency multiplexed, time multiplexed or have its transmit signal uniquely coded using one of various modulation schemes as known to those of skill in the art. These techniques could be used either alone or in combination to allow information for transmit/receive channels to remain distinct and are used in conjunction with careful antenna design and system layout to keep inherent crosstalk between channels to an acceptably low level.

In one embodiment, crosstalk is minimized by using high gain, directional antennas. In another embodiment, crosstalk is minimized by laying out antennas such that any sidelobe patterns do not intersect, i.e. alternating the orientation of adjacent antennas such that the radiation patterns between adjacent antenna pairs are rotated through 90°. In another embodiment, crosstalk is minimized by selecting an antenna pair with different polarizations to their neighbors, i.e. the first pair is horizontally polarized while the second pair is vertically polarized or the first pair is circularly polarized clockwise while the second pair is circularly polarized anti-clockwise. In another embodiment, crosstalk is minimized by shielding antennas from their neighbors using combinations of shielding and/or RF energy absorbing materials around each antenna.

Figure 18:
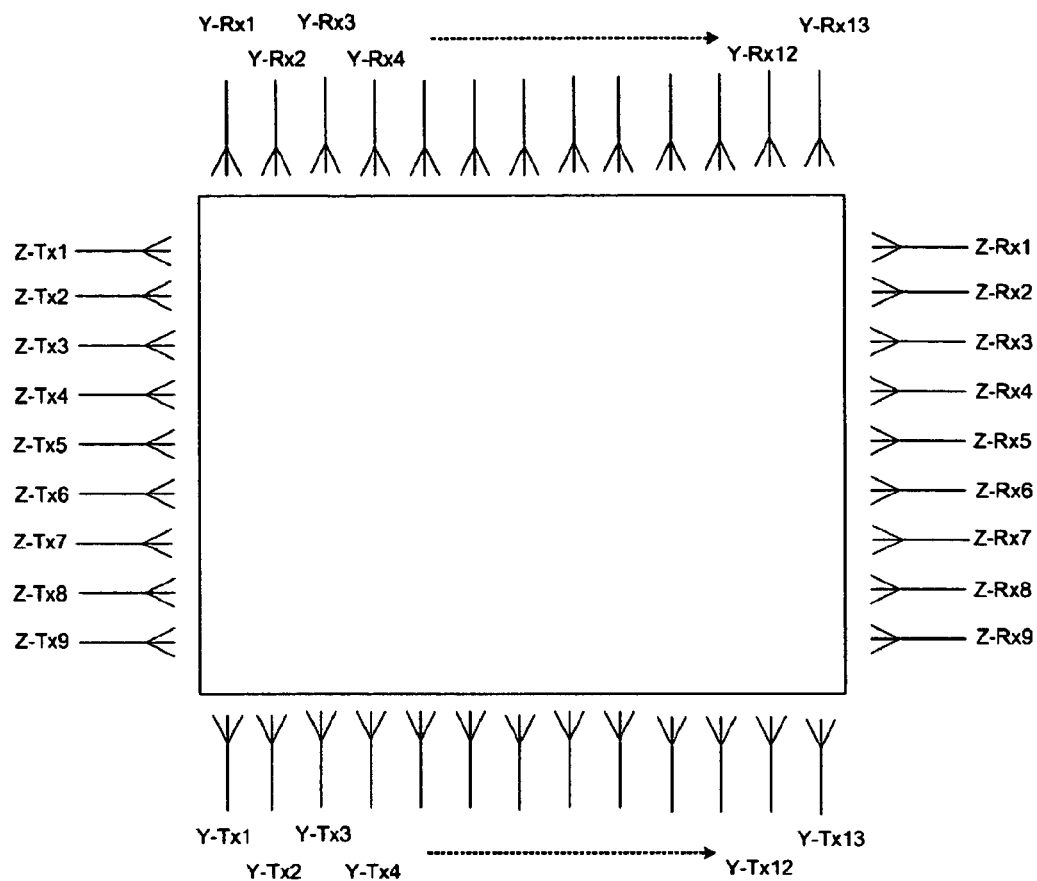
FIG. 18 depicts a preferred configuration of multiple antenna arrays in a two-dimensional imaging system.

As shown in FIG. 18, if multiple antenna arrays are used in more than one axis a calculation of the volume and shape of conductive items can be performed. This information can be used as part of an automated decision making process to determine whether a conductive item has the properties of a pre-determined threat type. In a preferred embodiment, the multiple antenna arrays are depicted as on both the y-axis and z-axis. The motion along the conveyor belt system is represented as an x-axis movement, while the multiple antenna arrays are represented as y-axis or z-axis measurements, with y-axis transmitter antennas matching to y-axis receiver antennas (i.e., Y-Rx1 aligned with Y-Tx1 upto Y-Rx13 aligned with Y-Tx13) and with z-axis transmitter antennas matching to z-axis receiver antennas (i.e., Z-Rx1 aligned with Z-Tx1 upto Z-Rx13 aligned with Z-Tx13). This calculation can be performed if the data from the various antenna pairs is passed to a computer via a suitable acquisition system, as are well known to those of ordinary skill in the art.

d. Microwave Imaging as Used in a Dual Stage System

As an alternate embodiment to using the microwave metal detection and imaging system of the present invention in a single stage, the microwave imaging system as described in the previous section may be employed as a first stage in the aforementioned dual stage scanning system. The microwave imaging system as the first stage can direct the scanning of the second stage.

The microwave imaging system of the present invention may be used in conjunction with and/or housed within a security system that uses one or more additional technologies to detect potential threats, including, but not limited to X-ray imaging systems, CT systems, x-ray diffraction systems, NQR systems, PFNA systems, TNA systems and explosive trace detection systems. Most or all of these systems can be incorporated into a conveyorised system. In typical systems, the conveyor will run through a tunnel. The tunnel may function as an RF shield in the case of an NQR system or as X-ray shielding in the case of an X-ray system, or both, but is not limited to such usage. Microwave imaging technology can be applied such that it is capable of operating within enclosed metallic tunnels. Metallic tunnels are typical of the architecture of X-ray, CT and NQR screening systems and hence the addition of shield detection, as in the microwave imaging system of the present invention, can be readily incorporated into the housing of a complimentary screening technology.

In an exemplary embodiment and referring back to FIG. 1, a dual stage scanning system 100 comprises a housing 130, which encompasses a conveyor system 115 for moving containers, baggage, luggage, or similar object 110 through a plurality of scanning stages 150, 155. In such preferred embodiment, the microwave metal detection and imaging system occupies first scanning stage 150. A sensor system 165 is connected at the entrance to determine when an object being scanned 110 enters the scan field and communicates with a controller [not shown] to activate or deactivate an X-ray radiation source, 170, 172, as needed. A lead lined tunnel 180 surrounds the conveyor to reduce radiation leakage outside the equipment. At least one radiation source is not expressly depicted in FIG. 1 and would be visible if the system were viewed from the opposite side.

e. X-Ray Transmission Combined with Microwave (Single Stage)

Figure 19:
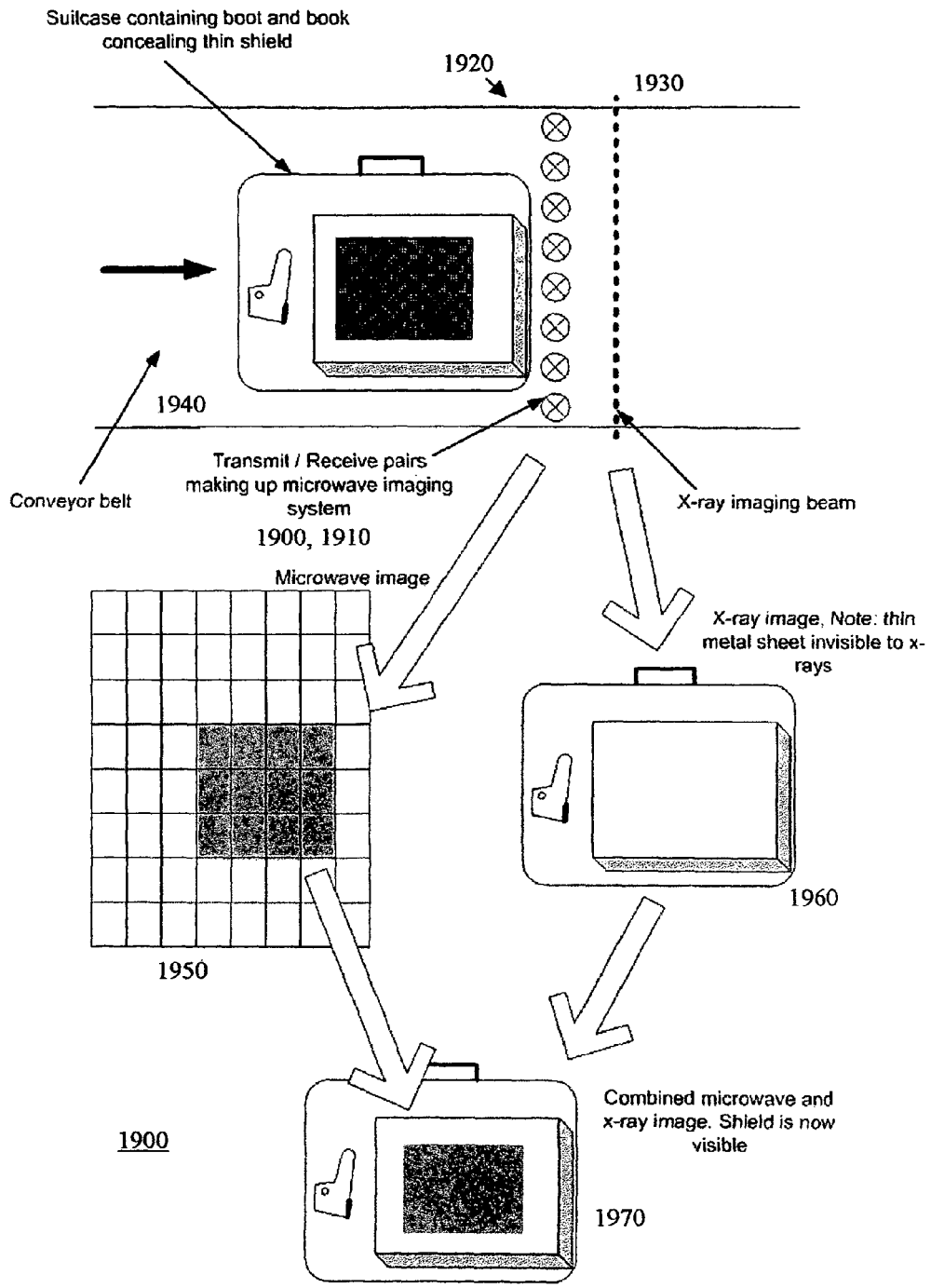
FIG. 19 illustrates a combined image derived from the image of the microwave imaging system and the image from an X-ray system, in another preferred embodiment of the present invention.

In another preferred embodiment, FIG. 19 illustrates an example of how the microwave imaging system of the present invention may be used in combination with an x-ray imaging system to overlay the image of thin (and therefore having low x-ray attenuation) conductive items that are not readily detectable using x-rays. The x-ray imaging system is thus enhanced by the ability to show a x-ray attenuation image combined with an electrical conductivity image (produced by the microwave system).

In a preferred embodiment, as shown in FIG. 19, the microwave imaging system 1900, comprised of transmit/receive antenna arrays 1910, is built into tunnel 1920, which would have a dual or multiple purpose (exemplary multiple purpose imaging machines are described further below) within the security system, and may include x-ray shielding or RF noise shielding for NQR security systems as described in detail above. The housing for the microwave imaging system would be small and would consist of opening 1930 in tunnel 1920 into which transmit/receive antenna arrays 1910 could be housed. Tunnel 1920 is lined with a material which does not attenuate microwaves significantly and allows for the inner walls of the tunnel to be smooth. The pitch between antenna pairs would be a function of the microwave frequency used along with the image resolution desired. This, in large part, depends on the object under inspection producing such image, and can include, but is not limited to baggage, carry on luggage, cargo or mail as well as the threat items that are being searched for during the inspection. While the object under inspection is passed through the security system via conveyor belt 1940, microwave image 1950 and X-ray image 1960 are produced. By using software processing techniques, microwave image 1950 and X-ray image 1960 are combined to produce combined image 1970.

In one embodiment, images are combined by displaying the X-ray image and visually defining the area containing metal using a translucent box having a different color or a different shade relative to the X-ray image. In another embodiment, images are combined by visually defining the area containing metal by drawing a plurality of lines around the perimeter of the detected metal volume, while retaining the x-ray image.

f. NQR Combined with Microwave

In an exemplary embodiment, the present invention employs a carefully designed microwave imaging system that is compatible with Nuclear Quadrupole Resonance (NQR) detection systems. NQR has shown significant potential for the detection of a range of materials, particularly, as described above, for the detection of the types of explosives that can be the most challenging to detect using x-rays or CT machines. One potential weakness of NQR, however, is that with carefully designed electromagnetic shielding the materials which the NQR technique is being used to detect can be rendered undetectable. The shielding effect can be mitigated by the fact that such shielding consists of conductive (typically metal) volumes which must completely encapsulate the item to be detected in order to mask it. Highly conductive material (for example, metal) can be used to enclose explosives and thus render the explosives undetectable using NQR.

In conventional systems, because the items being searched for are typically larger in size compared to most metal clutter, (i.e. keys, coins, zippers, etc) the counter measure can be detected using a variety of metal detection techniques. The presence of a conductive loop around much luggage, however, means that the simplest forms of inductive metal detectors would have limited performance.

Figure 20:
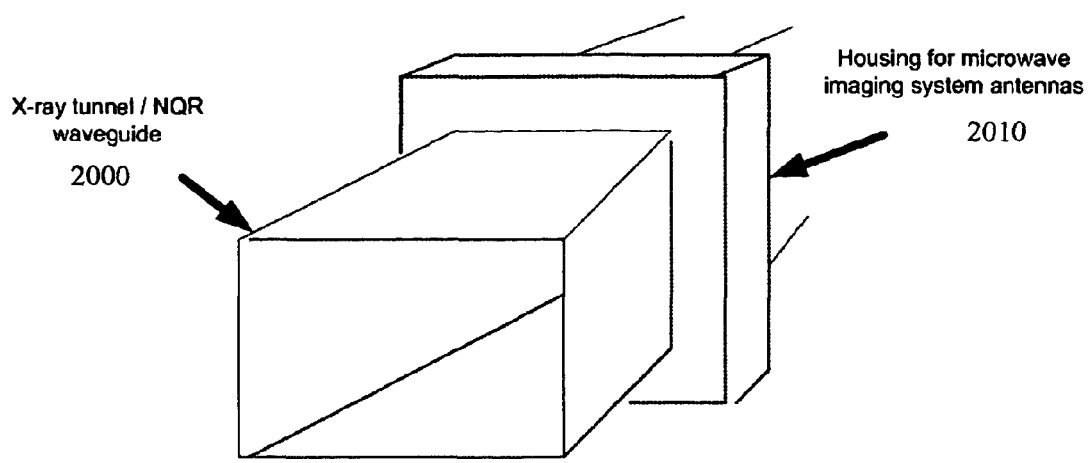
FIG. 20 is an isometric sketch depicting microwave antenna arrays housed in a system with a complimentary security technology, as in FIG. 17.

The microwave imaging system of the present invention may be incorporated into the NQR system as a shield detection system. FIG. 20 is an isometric sketch of the microwave imaging system described above with respect to FIG. 17, which can be housed in metallic tunnel 2000 that can also function as either the waveguide for an NQR system as described above or as the tunnel of an X-Ray/CT scan imaging machine. Metallic tunnel housing 2000 can be employed to save space required for a multi-technology system. In one embodiment, as shown in FIG. 20, housing for microwave imaging system antenna pair 2010 is arranged in a cutaway portion of metallic tunnel 2000. The microwave imaging system uses arrays of transmit/receive antenna pairs arranged around a conveyorised system to measure the conductive content of objects passing on a conveyor or equivalent transport mechanism.

Again referring to FIG. 20, the exemplary NQR security system as described with respect to FIGS. 11(a)-11(d) can comprise metallic tunnel 2000. The housing for microwave imaging system antennas 2010 is incorporated into this structure. The transmit/receive antenna pairs may be recessed within the metallic tunnels which are inherent to the structure of other detection technologies g. Other Detection Systems Combined with Microwave If the information from a conductive volume detecting system is combined with the result of a NQR scan, a result can be generated after the scan stating that the object under inspection is either clear, triggered a NQR alarm, or has areas that can be detected but not thoroughly inspected/interrogated. In the event that a detected area cannot be interrogated, the positional information for the shielded area can be transmitted to an imaging system (for example, but not limited to, CT or x-ray), which can direct the attention of an operator (or focus automated detection techniques) to the area that cannot be screened using NQR. This could be done by, for example, overlaying the metal image on the x-ray image.

Figure 21:
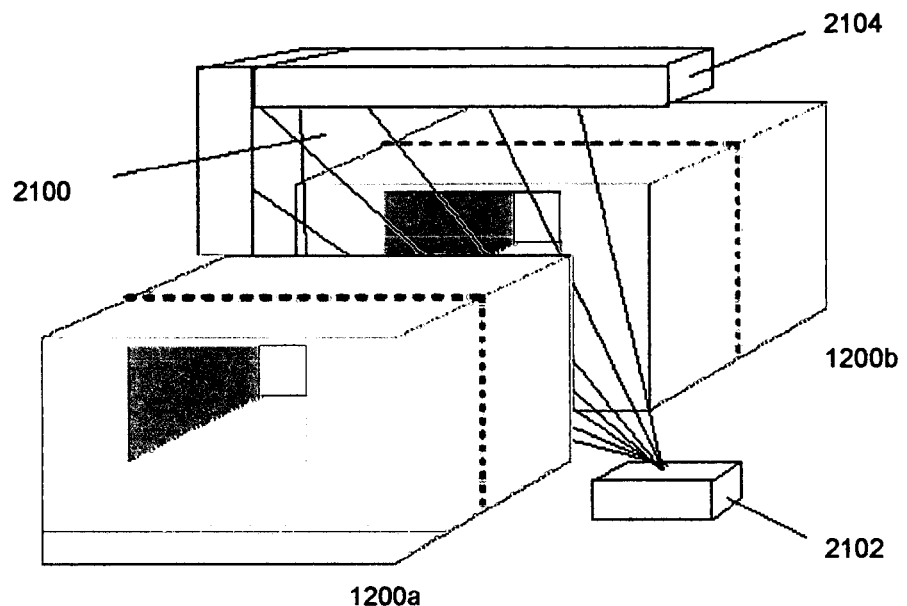
FIG. 21 is a diagram showing a baggage scanner configured to comprise two novel resonator probes and a transmission X-ray system in another embodiment of the present invention.

In another preferred embodiment of the present invention, a microwave imaging system is incorporated into an integrated multi-technology system, comprised of the NQR system described above and including, but not limited to imaging systems such as CT scanners and X-ray scanners. FIG. 21 depicts an example of an integrated multi-technology system. A line-scan X-ray system 2100, comprising X-ray generator 2102 and a folded array of L-shaped X-ray detectors 2104 is integrated with the dual coil NQR baggage scanner. Unlike conventional X-ray baggage scanners, NQR based baggage scanners only detect the presence of contraband in baggage without revealing their exact location in the baggage. Thus by integrating X-ray system 2100 with the NQR based scanner, the integrated scanning system will also be able to locate the contraband in the baggage. By further integrating the microwave metal detection and scanning system of the present invention into the NQR baggage scanning system, a shield detection system is incorporated, thus ensuring complete scanning of the object under inspection.

A line-scan X-ray system 2100 is provided in between the two resonator probes 1200a and 1200b. The fan shaped X-ray beams generated from X-ray generator 2102 scans the luggage passing through inspection volume 1104 on conveyor belt 1340 and impinges the X-ray detector 2104. The system is equipped with an alarm circuit, which will activate upon suspicion.

Figure 22:
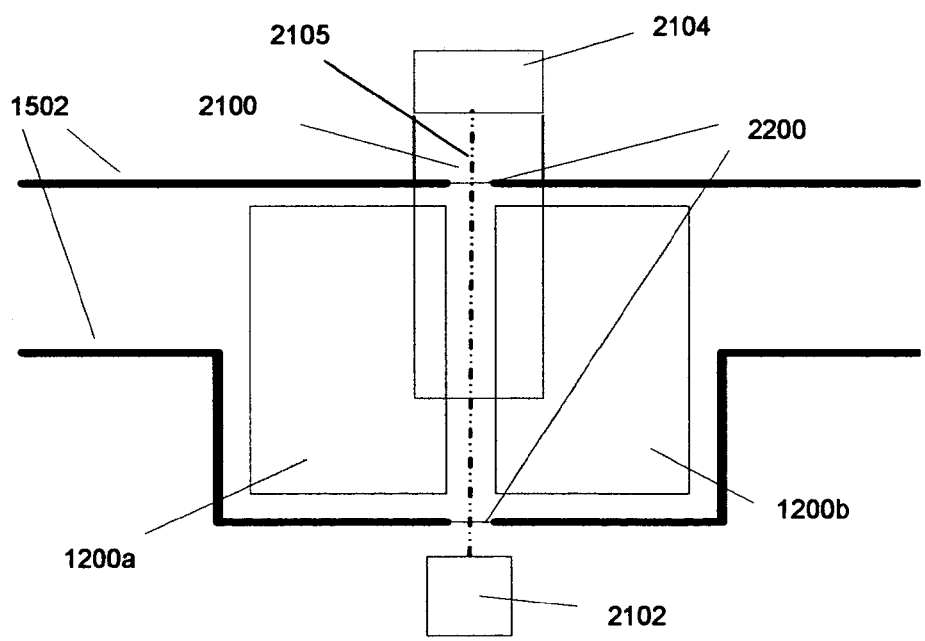
FIG. 22 depicts one embodiment of shielding for probes that have a thinned section of conductive material.

To allow CT scanners and/or X-ray scanners to be closely integrated to a produce a multi-technology system, it may be necessary to keep the X-ray or CT equipment outside of the electromagnetic shield used in conjunction with the resonator probe(s). Referring to FIG. 22, resonator probes 1200a and 1200b are surrounded by an electromagnetic shield 1502. The X-ray scanner 2100, having detectors 2104 and a X-ray source 2102, emits X-ray radiation. In order for the X-rays 2105 used by the CT or X-ray scanner 2100 to be allowed to pass through the electromagnetic shielding 1502 relatively un-attenuated, it is preferred that the shielding 2200 through which the X-rays 2105 are expected to pass is made of high conductivity material that is sufficiently thin and/or of a low density. The portion of electromagnetic shielding 2200 which offers low attenuation to X-rays could be integral to the rest of the shield or be an insert or inserts of thinner high conductivity shielding material such as aluminum which would minimally interrupt the x-ray beam 2105 between X-ray source 2102 and X-ray detectors 2104.

h. Further Examined by X-Ray Diffraction, Etc.

The inventions and embodiments thereof described here deal with a microwave imaging system, which can be used alone or in combination with one or a plurality of additional detection systems, allowing for the provision of three-dimensional positional information which can be transmitted to complementary detection sensors targeted at volumes within an object that cannot be screened effectively using NQR. In addition, a further use of the information from the conductive volume detecting system is to automatically direct material specific detection sensors which are not prone to masking by metallic shielding to the shielded volume. Examples of this type of technology include X-ray diffraction, thermal neutron analysis and pulsed fast neutron analysis.

i. Presentation of Imaging Information

Figure 23:
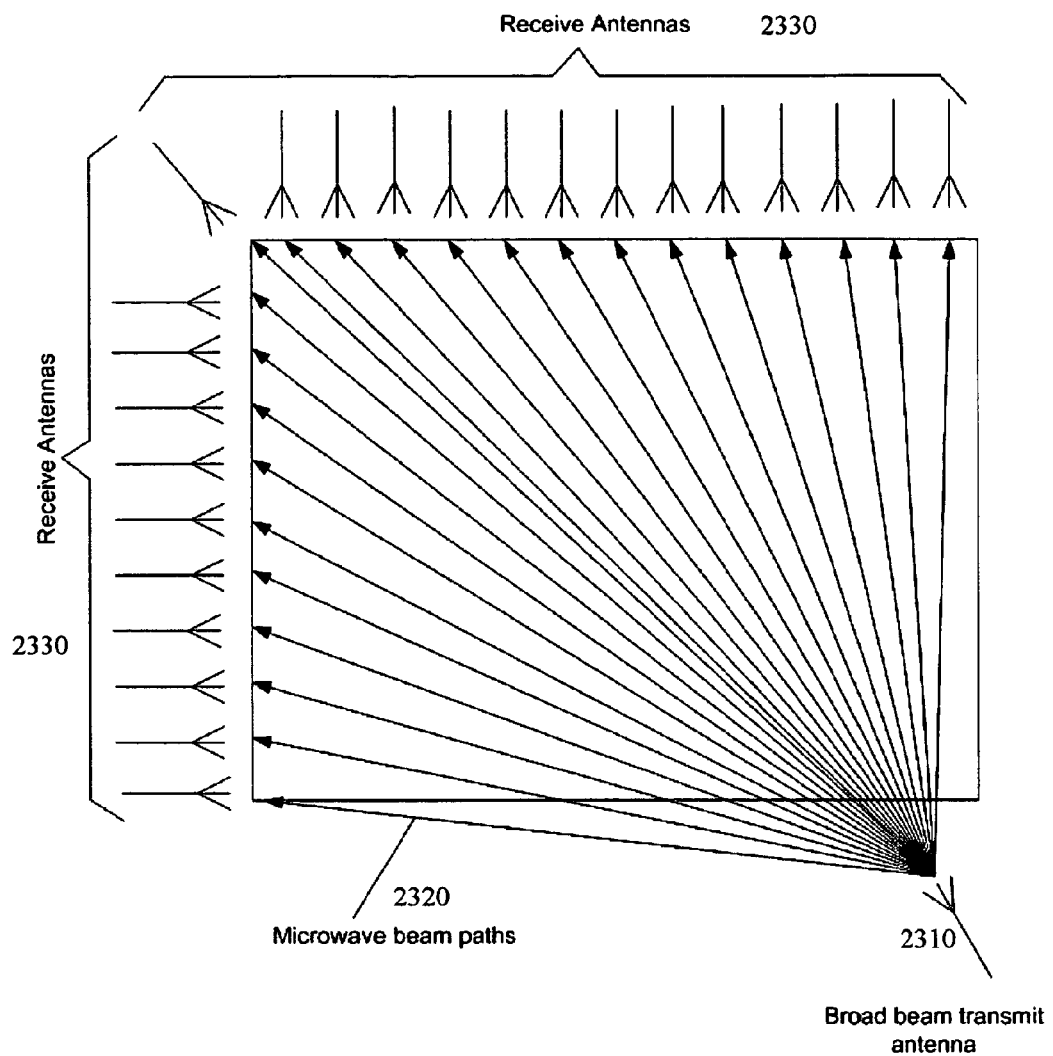
FIG. 23 illustrates a transmitted microwave fan beam and a folded array of detectors in a geometry typical of security line scan x-ray systems.

In another preferred embodiment of combined microwave and X-ray imaging systems, FIG. 23 depicts overlaid microwave and X-ray images. A single broad beam transmit antenna 2310 transmits microwave beam paths 2320 in a fan or cone-shaped radiation pattern and thus illuminates multiple receive antennas 2330. The position of the transmit antenna and the array of receive antennas can be such that it is similar to that of the x-ray generator and folded array of x-ray detectors in an x-ray imaging system. The layout, antenna type and switching order of transmit/receive pairs can be configured such that the microwave imaging system has the same geometry as the X-ray imaging system to which it is coupled, allowing for simple and accurate overlay.

Figure 24:
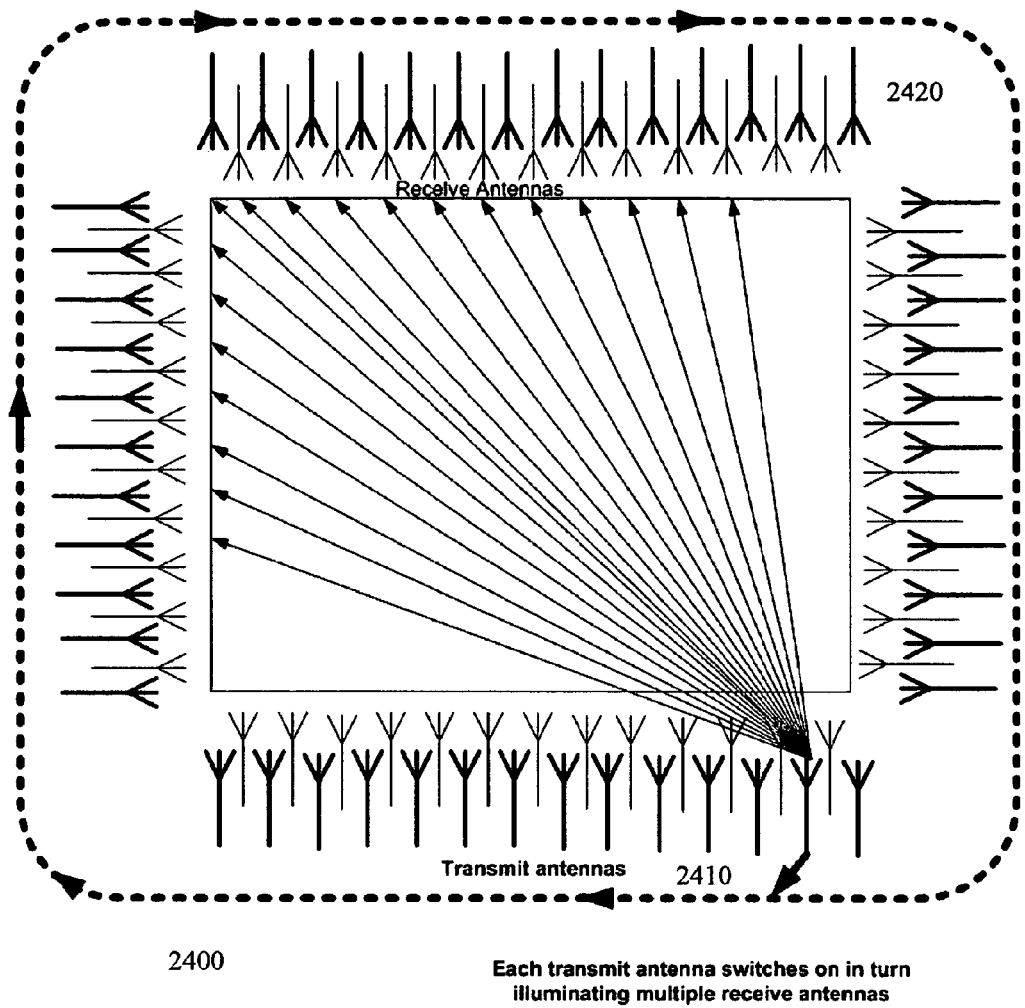
FIG. 24 depicts an exemplary configuration of transmit/receive antennas used to collect data producing CT images of conductive objects.

FIG. 24 illustrates yet another preferred embodiment of the present invention whereby the microwave imaging system is used to generate a computed tomography (CT) compatible image. In this embodiment, each transmit antenna can be activated in turn. Both the transmit antenna array 2410 and receive antenna array 2420 extend around the full perimeter of the system inspection tunnel 2400. Transmit antennas 2410 and receive antennas 2420 may be parallel and placed side-by-side, concentric, or any other similar geometry. It is also possible that each antenna may be used for both transmitting and receiving and switch between the two at appropriate times. In the preferred embodiment, a single antenna transmits a wide beam at any given time, thereby illuminating multiple receive antennas 2420. Transmit antennas 2410 sequentially switch on around the perimeter of tunnel 2400, thus, transmission takes place from each possible position around inspection tunnel 2400. This method allows for multiple transmission images for a given object to be generated at each angle. The received data from the receive antennas is processed for each transmission position creating a computed tomography image of the conductive contents of items under inspection. The information in theses images can be processed to develop computed tomography slices accurately showing the size, shape and position of conductive items within the inspection volume.

The above examples are merely illustrative of the many applications of the system of present invention. Although only a few embodiments of the present invention have been described herein, it should be understood that the present invention might be embodied in many other specific forms without departing from the spirit or scope of the invention. For example, while dual-stage scanning systems have been described with reference to first stage scanning systems comprising a dual-view line scanner and complimentary second stage scanning systems, comprising a transmission and scatter scan, other modifications and changes can be made by those of ordinary skill in the art. Additionally, while many of the systems described herein have been described with respect to use in dual stage scanning systems, it is to be understood that the embodiments described herein may be used as single stage scanning systems. Therefore, the present examples and embodiments are to be considered as illustrative and not restrictive, and the invention may be modified within the scope of the appended claims.

We claim:

1. A security scanning system, comprising:
    a first inspection system comprising:
        a housing that defines a tunnel and an inspection region;
        a conveyor that passes through said tunnel and defines a first direction through said inspection region;
        a first X-ray generator that projects a first fan of X-rays through a first slit collimator;
        a first detector array configured to receive said first fan of X-rays after they pass through said first slit collimator and said inspection region;
        a second X-ray generator that projects a second fan of X-rays through a second slit collimator, wherein said second X-ray generator is offset relative to the first X-ray generator in the first direction; and
        a second detector array configured to receive said first fan of X-rays after they pass through said second slit collimator and said inspection region; and
    a second inspection system comprising at least one of a NQR-based screening system, an X-ray transmission based screening system, an X-ray scattered based screening system, or a computed tomography based screening system.

2. The security scanning system of claim 1 wherein said first inspection system operates concurrent with said second inspection system.

3. The security scanning system of claim 1 wherein said first inspection system operates serially with respect to said second inspection system.

4. The security scanning system of claim 1 wherein said offset is approximately 100 mm.

5. The security scanning system of claim 1 wherein said second detector array is offset relative to the first detector array in the first direction.

6. The security scanning system of claim 4 wherein said offset is approximately 100 mm.

7. The security scanning system of claim 4 wherein said first detector array and said second detector array comprise 700 to 800 detectors.

8. The security scanning system of claim 1 wherein said first inspection system is configured to identify an item within said inspection region and determine an approximate centerline X-ray projection that passes through said item.

9. The security scanning system of claim 8 wherein said first inspection system is configured to extrapolate from said centerline X-ray projections physical coordinates of said item.

10. The security scanning system of claim 9 wherein said second inspection system uses said physical coordinates of said item to conduct a scan directed to a location derived from said physical coordinates.

11. A security scanning system, comprising:
    a first inspection system comprising:
        a housing that defines a tunnel and an inspection region;
        a conveyor that passes through said tunnel and defines a first direction through said inspection region;
        a first X-ray generator that projects a first fan of X-rays through a first slit collimator and that is positioned at a first angle relative to a perpendicular plane passing through a center of said conveyor; and
        a second X-ray generator that projects a second fan of X-rays through a second slit collimator, wherein said second X-ray generator is positioned on an opposite side of said conveyor relative to said first X-ray generator, wherein said second X-ray generator is positioned at a second angle relative to the perpendicular plane passing through the center of said conveyor, and wherein said first angle is equal to said second angle; and
    a second inspection system comprising at least one of a NQR-based screening system, an X-ray transmission based screening system, an X-ray scattered based screening system, or a computed tomography based screening system.

12. The security scanning system of claim 11 further comprising a first detector array configured to receive said first fan of X-rays after they pass through said first slit collimator and said inspection region.

13. The security scanning system of claim 11 further comprising a second detector array configured to receive said second fan of X-rays after they pass through said second slit collimator and said inspection region.

14. The security scanning system of claim 11 wherein said second X-ray generator is offset relative to the first X-ray generator in the first direction.

15. The security scanning system of claim 14 wherein said offset is approximately 100 mm.

16. The security scanning system of claim 11 wherein said first inspection system operates serially with respect to said second inspection system.

17. The security scanning system of claim 11 wherein said first inspection system operates concurrently with respect to said second inspection system.

18. The security scanning system of claim 11 wherein said first inspection system is configured to identify an item within said inspection region and determine an approximate centerline X-ray projection that passes through said item.

19. The security scanning system of claim 18 wherein said first inspection system is configured to extrapolate from said centerline X-ray projections physical coordinates of said item.

20. The security scanning system of claim 19 wherein said second inspection system uses said physical coordinates of said item to conduct a scan directed to a location derived from said physical coordinates.

* * * * *